United States Patent
Botto et al.

(10) Patent No.: US 9,335,273 B2
(45) Date of Patent: May 10, 2016

(54) APPARATUS AND METHODS FOR THE CHARACTERIZATION OF THE DIELECTRIC RESPONSE OF BOREHOLE FLUIDS USING A PHOTONIC BANDGAP MICROWAVE RESONANT CAVITY

(71) Applicant: SCHLUMBERGER TECHNOLOGY CORPORATION, Sugarland, TX (US)

(72) Inventors: Tancredi Botto, Cambridge, MA (US); Elizabeth Smythe, Cambridge, MA (US)

(*) Notice: Subject to any disclaimer, the term of this patent is extended or adjusted under 35 U.S.C. 154(b) by 305 days.

(21) Appl. No.: 13/791,455

(22) Filed: Mar. 8, 2013

(65) Prior Publication Data
US 2014/0252250 A1  Sep. 11, 2014

(51) Int. Cl.
| | | |
|---|---|---|
| G01N 21/85 | (2006.01) | |
| H01P 1/20 | (2006.01) | |
| G01N 21/954 | (2006.01) | |
| G01N 22/00 | (2006.01) | |
| G01R 33/00 | (2006.01) | |

(52) U.S. Cl.
CPC .............. *G01N 21/85* (2013.01); *G01N 21/954* (2013.01); *G01N 22/00* (2013.01); *G01R 33/0041* (2013.01); *H01P 1/2005* (2013.01)

(58) Field of Classification Search
CPC ........ G01N 22/00; G01N 21/954; G01F 1/74; G01F 1/58; G01F 1/584; G01F 1/66; G01F 1/6847; G01F 1/661; H01P 1/2005
USPC ............ 250/221, 573, 576, 227.18, 227.23, 250/227.25; 356/480; 324/633, 636, 634, 324/639, 637, 640; 385/2; 359/237, 245, 359/278, 315; 73/290 V
See application file for complete search history.

(56) References Cited

U.S. PATENT DOCUMENTS

| | | | | |
|---|---|---|---|---|
| 5,754,055 | A * | 5/1998 | McAdoo | G01N 33/2888 324/553 |
| 8,209,128 | B1 * | 6/2012 | Gourley | 702/19 |
| 8,692,183 | B2 * | 4/2014 | Csutak | 250/262 |
| 2007/0196043 | A1 * | 8/2007 | Peled et al. | 385/12 |
| 2009/0072744 | A1 * | 3/2009 | Botto | H05H 15/00 315/5.41 |
| 2009/0079976 | A1 * | 3/2009 | Cunningham et al. | 356/246 |

* cited by examiner

*Primary Examiner* — Que T Le
*Assistant Examiner* — Jennifer Bennett
(74) *Attorney, Agent, or Firm* — Daniel S. Matthews

(57) ABSTRACT

A method for characterizing the dielectric response of a fluid includes receiving the fluid into a portion of a flow line that is disposed proximate to a photonic bandgap (PBG) resonant cavity so that a dielectric permittivity of the fluid affects a frequency response of the resonant cavity. The method further includes providing electromagnetic waves to the resonant cavity and measuring a frequency response of the resonant cavity in the presence of the fluid in the flow line. The method further includes determining a property of a resonant mode of the resonant cavity using the frequency response and determining a property of the fluid using the property of the resonant mode.

24 Claims, 16 Drawing Sheets

US 9,335,273 B2

APPARATUS AND METHODS FOR THE CHARACTERIZATION OF THE DIELECTRIC RESPONSE OF BOREHOLE FLUIDS USING A PHOTONIC BANDGAP MICROWAVE RESONANT CAVITY

BACKGROUND

When an alternating electromagnetic field, such as a high-frequency microwave, interacts with a fluid, a host of dynamic polarization processes take place within the fluid. These processes depend, in part, on the complexity of the fluid and on the physical properties of the components (e.g., the complex permittivity) that make up the fluid. Dielectric relaxation due to the electric dipole re-orientation of the fluid atoms and/or molecules, in addition to ion conductivity effects, manifest themselves in the frequency dependence of microwaves that are transmitted or reflected from the sample.

The measured dielectric response is enhanced when the fluid under test passes through, or is housed within, a resonant cavity tuned to the desired measurement frequency, a process known as cavity-enhanced dielectric relaxation spectroscopy. Cavity-enhanced dielectric relaxation spectroscopy at high frequencies typically employs a metal-walled cylindrical resonator as the microwave cavity. The geometry of the resonator is chosen according to the desired operating frequency. Accordingly, the inner diameter of the cavity and, thus, the space available for a fluid sample under test is constrained by the chosen operating frequency. In a conventional metal resonator operating at 18 GHz, the peak of the resonant dielectric relaxation response of water, the presence of an opening for the fluid flow line or channel and the ohmic losses at the cavity metal walls limit the quality factor (Q-factor) of the cavity resonant mode to the order of 1,000. Dielectric interrogation of fluids at lower frequencies up to a few GHz typically does not employ resonant cavities but rather involve measurements across capacitor arms or measurements with electrodes invading the fluid volume.

Optical measurements are also deployed but, like low frequency microwaves, do not involve the use of cavity resonators. Optical measurements probe the much faster electronic transitions or molecular vibrational transitions of the sample.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, one or more embodiments of a system for characterizing a dielectric response of a fluid includes a photonic bandgap (PBG) resonant cavity having a resonant frequency. The resonant cavity is configured to be electromagnetically coupled to a flow line so that a fluid within the flow line affects a frequency response of the resonant cavity. A wave generator is electromagnetically coupled to the resonant cavity. The system further includes a signal analyzer configured to measure the frequency response of the resonant cavity.

In another aspect, one or more embodiments of a method for characterizing the dielectric response of a fluid includes receiving the fluid into a portion of a flow line that is disposed proximate to a photonic bandgap (PBG) resonant cavity so that a dielectric permittivity of the fluid affects a frequency response of the resonant cavity. The method further includes providing electromagnetic waves to the resonant cavity and measuring a frequency response of the resonant cavity in the presence of the fluid in the flow line. The method further includes determining a property of a resonant mode of the resonant cavity using the frequency response and determining a property of the fluid using the property of the resonant mode.

In another aspect, one or more embodiments of a system for characterizing a dielectric response of a fluid includes a generator for generating electromagnetic waves and a photonic bandgap (PBG) resonant cavity having a spatially localized resonant mode, wherein the resonant cavity is electromagnetically coupled to the generator. The system further includes a flow line disposed proximate to a photonic bandgap (PBG) resonant cavity so that the fluid contained within the flow line affects a frequency response of the resonant cavity. A signal analyzer configured to measure the frequency response of the resonant cavity is included in the system.

Other aspects and advantages of the disclosed subject matter of the application will be apparent from the following description and the appended claims.

DETAILED DESCRIPTION

The system and methods disclosed herein include systems and methods for characterizing the dielectric response of fluids. One or more embodiments disclosed herein employ high quality factor photonic bandgap (PBG) resonant cavities. One or more embodiments of the present disclosure relate to the characterization of the dielectric response of various borehole fluids, including drilling muds and production fluids (at the surface or in the subterranean borehole) as well as fluid sampled directly from the underground formation.

One or more embodiments may be applied to down-hole fluid sampling where the systems and methods may advantageously be able to determine the fraction of filtrate fluids in the flow line. Filtrates are complex mixtures of borehole drilling fluids that contaminate the sampling of the desired pristine formation fluids. Furthermore, one or more embodiments allow for the characterization of various multi-component fluids, e.g., formation fluids that include mixtures of gas, liquid, and crudes. Additional embodiments provide for a way to characterize the Saturates, Aromatics, Resins and Asphaltenes (SARA) content of a crude oil. One or more embodiments provide for a way to monitor drilling muds, e.g., changes in mud composition, such as changes in water fraction or salinity, may be monitored.

Figure 1:
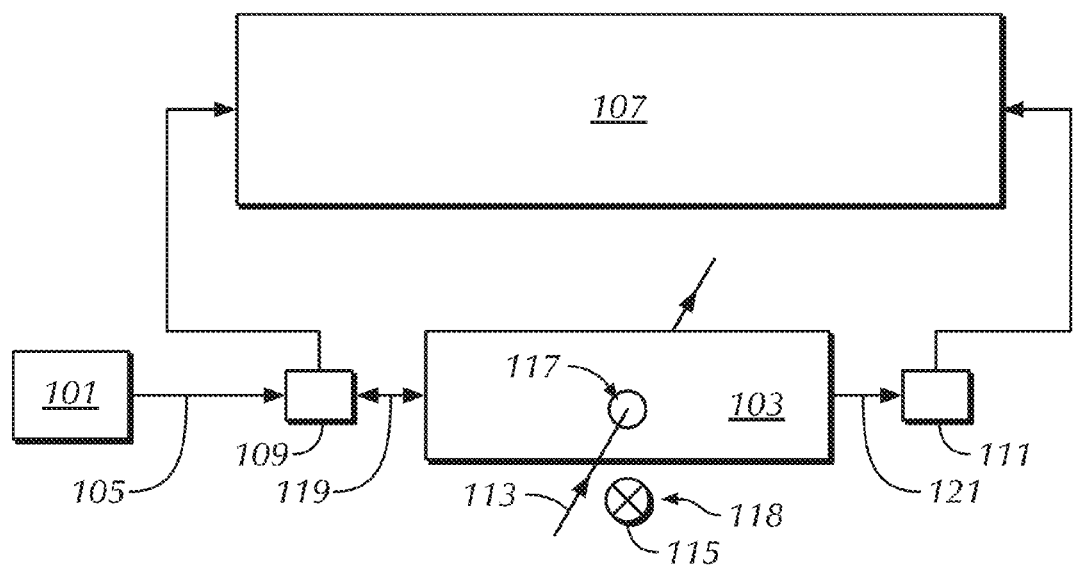
FIG. 1 shows an example of a system for characterizing the dielectric response of fluids in accordance with one or more embodiments.

FIG. 1 shows an example of a system for characterizing the dielectric response of fluids in accordance with one or more embodiments. The system includes signal generator 101 that is operatively connected to resonant cavity 103. More specifically, signal generator 101 is connected to resonant cavity 103 by way of interconnect 105. In accordance with one or more embodiments, the signal generator 101 is configured to generate electromagnetic waves in a particular range of frequencies, e.g., the microwave frequency range of 300 MHz to 300 GHz. Interconnect 105 directs these electromagnetic waves to the resonant cavity 103. In what follows, the example of signal generator 101 and resonant cavity 103 both operating near 17 GHz is described. However, one of ordinary skill will appreciate that any frequency of electromagnetic waves may be used, e.g., optical or terahertz waves, without departing from the scope of the present disclosure. Furthermore, interconnect 105 may be any interconnect known in the art, e.g., coaxial cabling, hollow waveguides, striplines or the like.

In accordance with one or more embodiments, resonant cavity 103 is a microwave resonant cavity, by which is meant that the resonant cavity includes at least one resonant mode in the microwave frequency range, near 17 GHz in this example. Furthermore, in accordance with one or more embodiments, the resonant cavity 103 is formed from a meta-material having a photonic band-gap due to an internal structure formed from a periodic arrangement of materials having dissimilar dielectric permittivity $\in$, as is described in more detail below in reference to FIGS. 2-4. Furthermore, in accordance with one or more embodiments, the electromagnetic field from the resonant mode of resonant cavity 103 is largely spatially localized near a region 117 within the resonant cavity 103. However, the spatial extent of the resonant mode of resonant cavity 103 may extend to regions outside of resonant cavity 103, that is to say that the electromagnetic field of the resonant mode extends to a region 118 near to, but outside of, the resonant cavity 103.

In accordance with one or more embodiments, a signal analyzer 107 is operatively coupled to the microwave resonant cavity 103 and is configured to measure the microwave signal 119 that is reflected from microwave resonant cavity 103 and/or is configured to measure the microwave signal 121 that is transmitted through microwave resonant cavity 103. More specifically, in accordance with one or more embodiments, a coupler 109 may be installed along interconnect 105 so as to direct any reflected microwave signals to the signal analyzer 107. Similarly, in accordance with one or more embodiments, a coupler 111 may be installed at the output of resonant cavity 103 so as to direct any transmitted microwave signals to the signal analyzer 107.

In accordance with one or more embodiments, the system may be configured to make what is known as an S12 measurement using the signal analyzer 107. For example, signal analyzer 107 is configured to measure both the incoming signal to the resonator at coupling port 109 and the transmitted signal emerging from the resonant cavity at the far coupling port 111. One of ordinary skill will appreciate that the system may be configured to equivalently make an S21 measurement by swapping ports 109 and 111 without departing from the scope of the present disclosure. In addition, in accordance with one or more embodiments, the analyzer 107 may be configured to make a single port S11 (or S22) measurement by measuring both the incoming and reflected signal from port 109 (or port 111) by way of e.g., interconnects 123 and 125. One of ordinary skill will appreciate that phase detection for either a transmission or reflection measurement depends on how the signals are handled in the signal analyzer 107. For example, to retain phase information, any input signal to signal analyzer 107 is processed by a quadrature splitter to separate the real and imaginary wave amplitudes.

A variety of methods may be used to couple the electromagnetic waves into or out of the resonant cavity 103. For example, waveguides, horns, or loop couplers at the end of a coaxial cable may be deployed or integrated into the input and output ends of the resonant cavity 103 to ensure efficient coupling of the electromagnetic waves into or out of the resonant cavity 103.

In accordance with one or more embodiments, the signal generator 101 is configured to generate a microwave signal having arbitrary frequencies thereby allowing for a sweep, "chirp," or arbitrary choice for the frequency of the generated electromagnetic wave. In still other embodiments, the signal generator 101 may be integrated with, or otherwise part of the signal analyzer 107, e.g., the signal analyzer may be a vector network analyzer, or the like. Such arbitrary multi-frequency generation capability allows for the amplitude and/or phase of the transmitted and/or reflected electromagnetic waves to be measured by the signal analyzer 107 as a function of frequency, thereby forming a reflection or transmission spectrum (both of which are encompassed within the term frequency response, as used herein) of the resonant cavity 103. In accordance with one or more embodiments, the reflection or absorption spectrum is characterized by a resonant frequency $f_0$ and resonance width $\Delta f$. The resonance frequency $f_0$ generally corresponds to the frequency of at least one of the resonant modes of the resonant cavity 103 and the resonance width $\Delta f$ of the spectrum generally inversely corresponds to the quality factor (Q-factor) of said resonant mode, where the Q-factor is defined as $f_0/\Delta f$.

The system for characterizing dielectric response of fluids further includes a fluid flow line for containing the fluid under test. The fluid flow line may pass through the resonant cavity 103, as shown by flow line 113 and/or may be positioned outside of the resonant cavity 103, as shown by flow line 115 with a flow direction pointing into the page. Accordingly, the fluid under test may flow through, or be introduced into, the resonant cavity 103 or flow near, or be introduced near, the microwave resonant cavity 103 along the flow lines 113 and/or 115, respectively. One of ordinary skill will appreciate that the fluid under test may be continuously flowing through the flow line during a measurement or may be introduced into the flow line but be stationary during a measurement. In other words, the term "flow line" should not be limited to a conduit, pipe, or tube that continuously passes the fluid under test therethrough, but rather, should be construed to also include any container or vessel that may receive and contain a fluid. In accordance with one or more embodiments, the flow line may be formed from a low-loss, dielectrically transparent material such as quartz or sapphire or, e.g., a ceramic material. In addition, the flow line may be a void or hole in the material of the resonant cavity 103 in which case the walls of the flow line are formed of the same material as the resonant cavity, as is described in more detail below. In yet another embodiment, more than one flow line may be employed. For example, an additional flow line containing a known reference fluid for cross check and calibration may be employed.

Generally speaking, and discussed in more detail below, the presence of fluid in the flow lines 113 and/or 115 will produce a measurable effect on both the resonant frequency and the Q-factor of the resonant cavity 103, and thus, these parameters, as measured by a reflection or transmission spectrum may be used to characterize the properties of an unknown fluid in the flow line 113 and/or 115. For example, in accordance with one or more embodiments, the volume fraction of the various components that make up the fluid can be determined. This is the case with a variety of borehole fluids, including drilling muds and production fluids (at the surface or in subterranean boreholes) as well as fluid sampled directly from an underground formation. When passing through or near resonant cavity 103, borehole fluids primarily containing hydrocarbons will give a generally weak background dielectric response. However, in some cases, borehole fluids may also have a significant volume fraction of components with a strong dielectric response, such as water and brines. The dielectric response of drilling muds can be fine-tuned to provide a unique tag for different additives to a drilling fluid, including alcohols (commonly used to prevent hydrate formation), nanoparticles, and other additives containing polar molecules, such that any contamination from drilling fluids in the sample can be monitored.

Figure 2A:
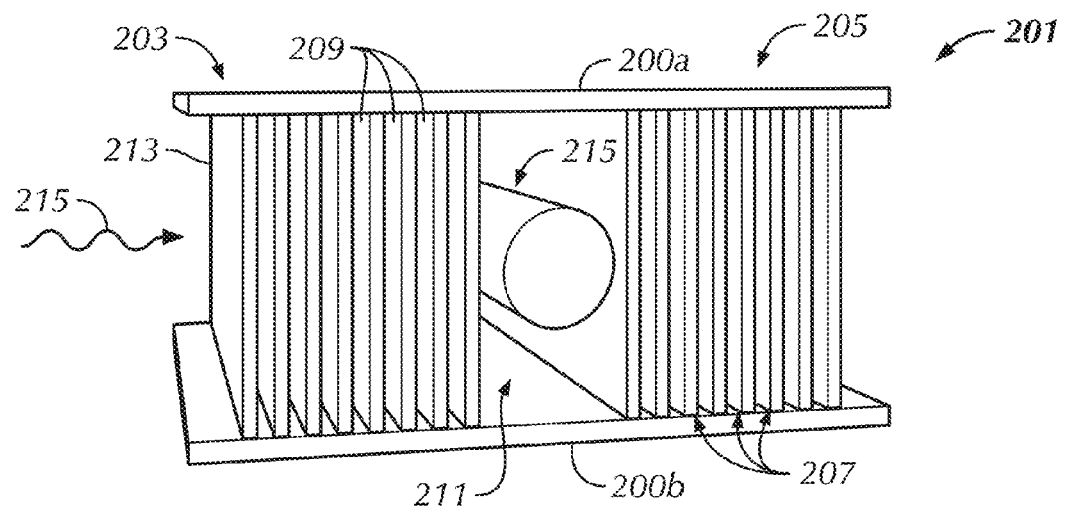
FIGS. 2A-2B show examples of photonic bandgap resonant cavities in accordance with one or more embodiments.

FIG. 2A shows an example of a photonic bandgap (PBG) resonant cavity 201 in accordance with one or more embodiments. More specifically, FIG. 2 shows an example of a PBG resonant cavity based on a pair of planar Bragg mirrors, also known as distributed Bragg reflectors. In this example, the PBG resonant cavity 201 includes Bragg mirrors 203 and 205 sandwiched between end plates 200a and 200b. As used herein, the term Bragg mirror is used to refer to a 1D photonic crystal formed from a periodic stacks of materials alternating between high and low permittivity. In the embodiment shown in FIG. 2, the Bragg mirror is constructed from layers of ceramic plates 207 separated by equally spaced air gaps 209. For clarity only a subset of the plates and air gaps are labeled in the figure. When a microwave frequency of a certain frequency propagates through this periodic system, each air/ceramic layer boundary causes a partial reflection of the microwave. For waves whose wavelength is close to four times the optical thickness of the layers, the many reflections combine with constructive interference, and the layers act as a high-reflectance reflector. The range of wavelengths that are reflected is called the photonic stopband or bandgap. Within this range of wavelengths, the electromagnetic field is "forbidden" to propagate in the structure. Accordingly a very high reflection coefficient may be obtained with a moderate number of plates 207. While the example shown in FIG. 2 shows air gaps separated by ceramic plates, one of ordinary skill will appreciate that the device may comprise plates of any material and may include alternating plates of different material as opposed to the alternating plate-gap configuration shown in FIG. 2.

The Bragg mirrors 203 and 205 are arranged with a defect (or gap) 211 between them. Thus, because mirrors 203 and 205 are highly reflective, the defect 211 serves as a microwave cavity that traps the microwaves in a spatially localized resonant mode within defect 211. In accordance with one or more embodiments, one or more spatially localized resonant modes having frequencies within the bandgap of the photonic crystal can exist in the volume of the defect 211. Thus, a microwave 215 having a frequency within the bandgap that is coupled at one end 213 of the PBG resonant cavity 201 will travel through the Bragg mirror 203, partially reflecting off of each interface until a fraction of the wave reaches the defect 211, also referred to herein as the cavity volume, where it is trapped by the two high reflectivity Bragg mirrors 203 and 205, thereby forming a spatially localized mode. However, microwaves at a non-resonant frequency, including microwaves outside the bandgap will either be reflected back or travel through the Bragg mirrors 203 and 205 unimpeded and, thus, these waves do not contribute to the localized resonant mode. The electromagnetic confinement mechanism is based on the geometrical properties of the photonic crystal and, thus, such a device can be built entirely of low loss dielectric materials thereby creating a resonant cavity having intrinsically small wall losses and a high Q-factor.

In accordance with one or more embodiments, a flow line 215 is disposed near the defect 211. In the example shown in FIG. 2A, the flow line 215 is disposed within a central region of the defect 211 to allow for optimum overlap of the internal volume of the flow line with the center of the localized resonant mode located within the defect 211. However, other configurations are possible without departing from the scope of the present disclosure. For example, the center of flow line 215 may be offset from the center of defect 211 or the flow line 215 may be located completely outside but still close enough to the defect region so as to couple to, and thereby affect, the frequency response of PBG resonant cavity 201. In accordance with one or more embodiments, a presence of a fluid in the flow line 215 results in a dielectric load that minimally perturbs the cavity performance, but nevertheless, results in a measurable change in the resonance properties of the PBG resonant cavity 201. More specifically, the resonance frequency and Q-factor of the resonant modes of the cavity will be affected by the presence of fluid in the flow line 215. Accordingly, a measurement of the resonance frequency and Q-factor of at least one resonant mode of the cavity allows for a characterization of a number of properties of interest of fluids under test, as described in more detail below.

Figure 2B:
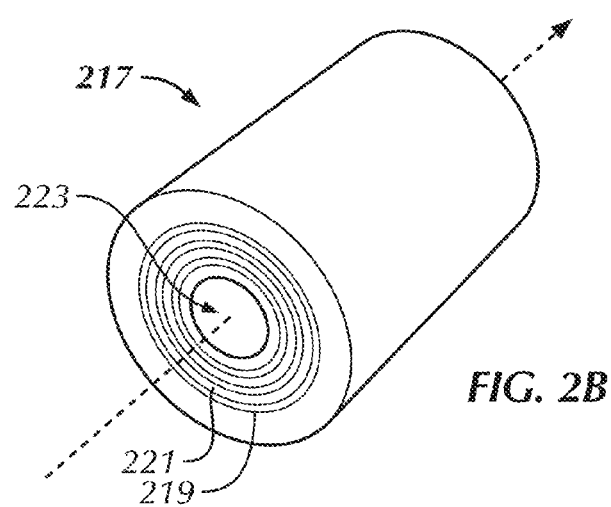

FIG. 2B shows an example of a PBG resonant cavity 217 in accordance with one or more embodiments. More specifically, FIG. 2B shows a device that is similar to FIG. 2A described above in that the system is formed from a 1D photonic crystal of alternating layers 219 and 221 having alternating high and low permittivity. However, FIG. 2B is formed having a cylindrical symmetry so that each layer is formed as a concentric cylindrical shell that surrounds defect (or hollow core) 223, giving rise to a cylindrical Bragg mirror. As before, a localized resonant mode is confined within the defect 223, which is formed as a hollow core along the length of the bandgap resonant cavity 217. This hollow core may itself serve as the flow line for introducing an unknown fluid into the PBG resonant cavity 217 for test. Alternatively, a tube may be inserted (not shown) into the defect 223 and thereby may operate as the flow line.

Figure 3A:
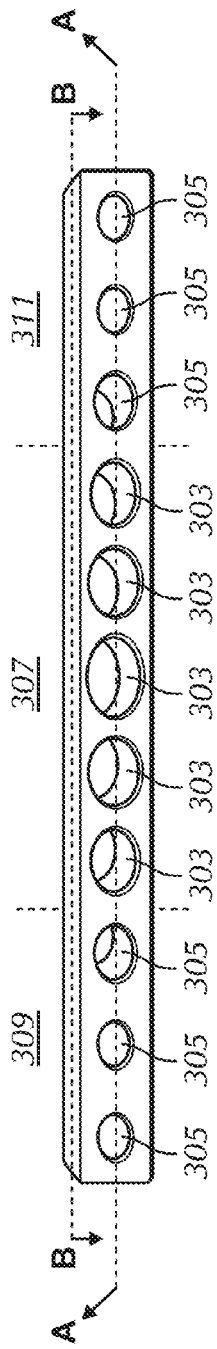
FIGS. 3A-3C show examples of photonic bandgap resonant cavities in accordance with one or more embodiments.
Figure 3B:
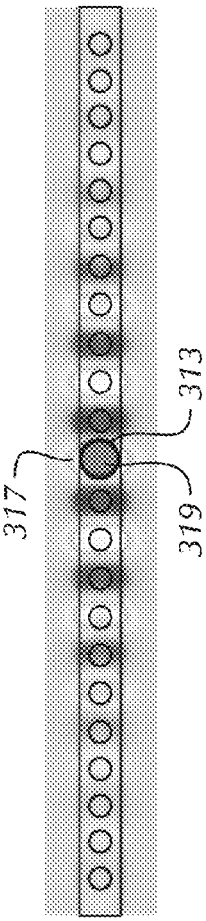
Figure 3C:
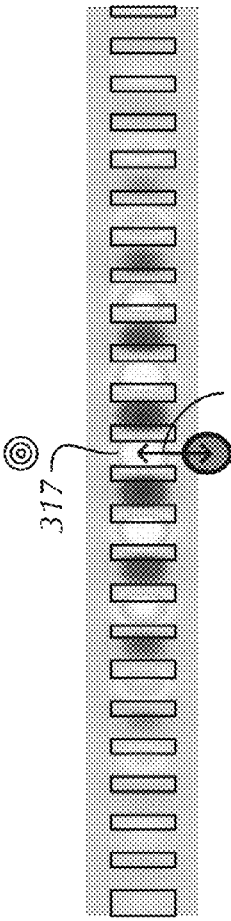

In another example, the stack of alternating high and low permittivity materials giving rise to the 1D photonic crystal may be realized not strictly as a stack of layers but as a bulk dielectric material having a series of holes with a given spacing and geometry that are drilled, etched, or ablated from the bulk material. Such a cavity is shown in FIGS. 3A-C. In the PBG resonant cavity 301, the permittivity modulation, e.g., the alternating high-low permittivity structure, is given by the succession of segments formed from the bulk material (e.g., the high permittivity material) and the segments where the permittivity of the same bulk material is lowered by the presence of a hole, including, e.g., an air filled hole. Furthermore, the PBG resonant cavity 301 includes a bulk material having cavity region 307 with multiple holes bored therethrough 303. For example, in accordance with one or more embodiments, the total number of holes in the cavity region is about 20 (not shown for the sake of clarity). However, any number of holes may be used without departing from the scope of the present disclosure. In addition, the cavity region is abutted on either side by Bragg mirror sections 309 and 311, each including a series of holes 305. For example, in accordance with one or more embodiments, the total number of holes in the each Bragg mirror section is about 10 (not shown for the sake of clarity). However, any number of holes may be used without departing from the scope of the present disclosure. Furthermore, in accordance with one or more embodiments, the diameters and/or positions of the holes in the bulk material are varied along the length of the bulk material in order to advantageously focus the cavity resonant mode over a small volume or to optimally confine the resonant mode to one of the air regions defined by the presence of a hole. In accordance with one or more embodiments, the PBG resonant cavity 301 is designed to operate at a frequency near 17 GHz. Thus, in order to design a PBG resonant cavity, the alternating high and low permittivity layers, and therefore the diameter of the holes may be of the order of ¼ the wavelength or less, e.g., 0.50 cm or less.

More specifically, in accordance with one or more embodiments, for a bulk material made from alumina ($Al_2O_3$) ceramic that is 9 mm thick and 4.5 mm wide, typical holes may have approximately 3 mm diameter and hole centers may be 4-5 mm apart. However, the hole size and spacing, as well as the slab dimension, depend not only on the operating frequency, but also on the value of permittivity of the substrate bulk material chosen. For instance, for the same 17 GHz resonator shown in FIG. 3, but built out of a higher permittivity ceramic, the corresponding hole size and spacing would be smaller. Furthermore, in accordance with one or more embodiments, the number of Bragg mirror regions depends primarily on the ratio of the permittivities between the high and low permittivity materials $\epsilon_1/\epsilon_2$. A larger $\epsilon_1/\epsilon_2$ results in a larger reflectivity of the Bragg mirror for a given number of holes (or slabs). Accordingly, a higher $\epsilon_1/\epsilon_2$ ratio calls for a lower number of holes (or slabs) to form an effective Bragg mirror. For example, for an $Al_2O_3$ slab ($\epsilon_1$=9.3-11.5) having air filled holes ($\epsilon_2$=1), to form a 17 GHz resonator about 10 mirror sections per side are suitable. In addition, in this example 9 holes per side, with each hole having gradually increasing diameter towards the central cavity hole, may provide a transition region from the mirror section to the central cavity hole. For example, in accordance with one or more embodiments, 10 equal diameter Bragg-mirror holes each of 2.8 mm diameter and spaced approximately 4.5 mm apart are used to form the mirror sections. To form the cavity region, 9 tapered cavity holes with their diameter and spacing gradually increasing are formed in combination with a central cavity hole of 3.05 mm diameter.

FIGS. 3B-3C show electric field contour plots of the localized resonant mode within the cavity regions of a 1D photonic resonant cavity similar to that described above in reference to FIG. 3A. The spatial structure of the resonant mode includes a series of maxima and minima in the electric (or magnetic) field wherein the amplitude of these maxima and minima decay along the length of the cavity from central maxima 317 toward the Bragg reflector regions (not shown). Accordingly, the mode is said to be spatially localized near the center of hole 313. FIG. 3B shows a contour plot of a cross section of the resonant cavity shown in FIG. 3A, cut along the line B-B. FIG. 3C shows a contour plot of a cross section of the resonant cavity shown in FIG. 3A, cut along the line A-A.

As is shown in FIGS. 3B-3C, the spatial extent of the localized resonant mode may extend outside of the cavity bulk material. Thus, not only may the flow line 319 be placed inside the cavity itself, e.g., within hole 313, but, in accordance with other embodiments, the flow line 319 may be placed outside the cavity, at a distance z from the localized mode. One of ordinary skill will appreciate that the particular design of the PBG resonant cavity and the choice of PBG materials will affect the spatial extent of the localized resonant mode, and, thus, the distance z may be tailored depending on the design constraints of the system. Further, in accordance with one or more embodiments, one or more flow lines may be located inside one or more holes that may, or may not be, holes that correspond to the location of the maximum field intensity for the resonant mode. In yet other embodiments, one or more flow lines may be placed near the cavity itself but not necessarily located within a hole. Likewise, any hole in the bulk material itself may be used for a flow line without the need for a separate vessel for containing the fluid under test. Accordingly, the PBG resonant cavity 301 makes for a versatile resonant cavity to be employed in a system for characterizing the dielectric response of a fluid in accordance with one or more embodiments.

While FIG. 3 shows a system deploying holes in a bulk material, a system that deploys regularly or periodically spaced rods in a bulk dielectric material may also be used without departing from the scope of the present disclosure. Furthermore, the rods may be filled or formed with a material having permittivity that is either lower or higher than the bulk material permittivity. For, example, the rods may be formed of a metal and/or ceramic material. One may also create defects using special geometry rods, such as hollow rods, split-rods, partially withdrawn rods or rods with different geometries. The frequency of the spatially confined mode of the microwave field depends on rod spacing, diameter and shape, as well as rod placement and overall cavity geometry.

Figure 4A:
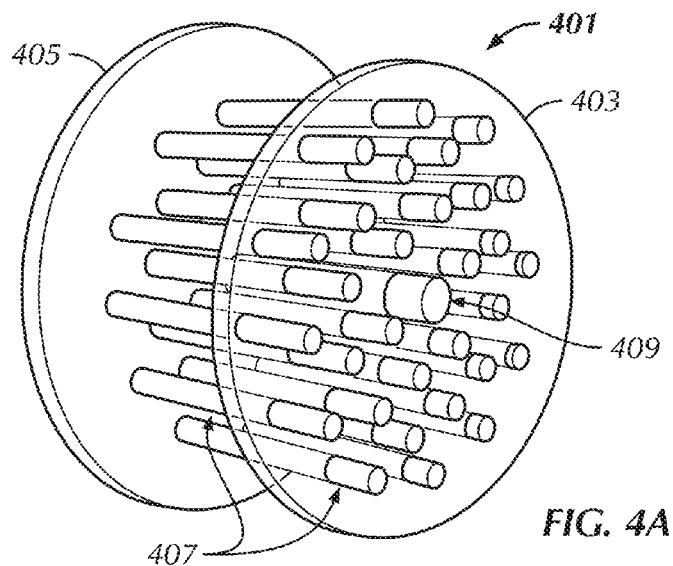
FIGS. 4A-4B show examples of photonic bandgap resonant cavities in accordance with one or more embodiments.

Another class of suitable resonators are 2D photonic crystals, an example of which is shown in FIG. 4A. The 2D photonic crystal 401 includes two end plates 403 and 405 between which run an array of regularly or periodically spaced dielectric or metal rods 407. The end plates 403 and 405 of the cavity are typically parallel to each other and may have a round or any other cross section. The rods 407 may have circular, elliptic or other cross-sections, including varying cross sections. In addition, the volume between the endplates 403 and 405 and may be fully or partially enclosed by exterior walls or enclosed in a separate chamber superstructure. In accordance with one or more embodiments, the flow channel 409 may be one of the rods 407 modified to carry a fluid, or, e.g., may be a hollow tube or vacancy in the bulk material running the length of the cavity.

In accordance with one or more embodiments, the 2D spatial arrangement of the permittivity function of the crystal may be arranged to give rise to a bandgap. Furthermore, when a defect, such as a missing rod or hollow rod is introduced, a cavity is created and a spatially confined mode of the microwave field will be localized within this defect region. While FIG. 4 shows a system deploying rods, a system that deploys regularly or periodically spaced holes in a bulk dielectric material may also be used without departing from the scope of the present disclosure. Furthermore, the holes may be filled with a material having permittivity that is either lower or higher than the bulk material permittivity. For, example, the rods may be formed of a metal and/or ceramic material. One may also create defects using special geometry rods, such a hollow rods, split-rods, partially withdrawn rods or rods with different geometries. In accordance with one or more embodiments, functionalized hollow rods may also be used. For example, such a functionalized rod would have a cavity response that may be tuned or varied depending on the rod filler material, e.g., by using a liquid with a specific complex permittivity value. The frequency of the spatially confined mode of the microwave field depends on rod spacing, diameter and shape, as well as rod placement and overall cavity geometry. For example, at 10 GHz frequencies, the spacing between the rods may be 15-20 mm for rod diameters of a 3-5 mm. Generally, operating at higher frequencies will involve smaller distances and diameters.

In accordance with one or more embodiments, the plates, rods and walls, or parts thereof, may be formed from metallic conductors, dielectric insulators or coated metals or insulators, or a combination of metallic and dielectric elements. Use of rods or end plates made of dielectric material with very low loss factors in the frequency region of interest (10's of GHz) such as Alumina ($Al_2O_3$) or single crystalline sapphire minimizes losses and improves the Q-factor. The overall Q-factor in a cavity is limited by its intrinsic Q-factor, before dielectric or ohmic losses, which is typically very high (Q~up to $10^6$). By minimizing ohmic and dielectric losses the Q-factor approaches its high intrinsic value.

In accordance with one or more embodiments, to optimize losses and/or to tailor the bandgap resonant frequency, the rods may be of different materials, and the cavity may be partially or fully loaded with a dielectric medium. Hollow rods with cooling help reduce the dielectric loss-tangent. Such fine tuning could be also advantageous to better shape the electric field and/or improve mode selection inside the cavity, and finally to optimize the cavity dimensions and operating frequency with respect to the constraints typical of borehole tools In accordance with one or more embodiments, 1-D and 2-D PBG resonant cavities may be formed of a periodic arrangement of materials having dissimilar complex permittivities. As used herein, the term complex permittivity includes a real part representing the dielectric permittivity of the material and an imaginary part representing the conductivity of the material. For example, the complex permittivity of a material may be expressed as $$\varepsilon_{complex} = \varepsilon + i\frac{\sigma}{\omega \varepsilon_0},$$

where $\in$ is the real part of the permittivity and $\sigma$ is the conductivity of the material. Accordingly, the periodic arrangement may include materials having dissimilar dielectric permittivities and/or conductivities.

A band-gap inside a perfect, i.e., infinite, PBG resonant cavity might not be coupled to an electromagnetic wave incident from outside the cavity. Accordingly, in certain embodiments it may be possible to realize a practical PBG resonator within either a dielectric or hollow metal waveguide that supports the propagation of certain waveguide modes that correspond to the frequency of the cavity mode. In certain other embodiments, in order to couple the cavity to an external excitation source, some of the elements of the periodic PBG structure (e.g., rods from the external rows in FIG. 4) may be removed or partially withdrawn. Alternatively, one may use thinner diameter rods. This does not significantly affect the field in the central region, which to first order is shaped by the inner rows of rods, whereas the outer rods provide focusing and confinement of the mode in the central defect region. Coupling to the external source may also be achieved with a coupling loop at the end of a coaxial transmission line, including a balanced transmission line. Alternatively, a specially designed waveguide can be employed to obtain an effective proximity coupling with the PBG resonant cavity. At very high operation frequencies (100 GHz or more) an equivalent PBG structure may be manufactured through micro or nano-fabrication (MEMS) techniques.

Figure 4B:
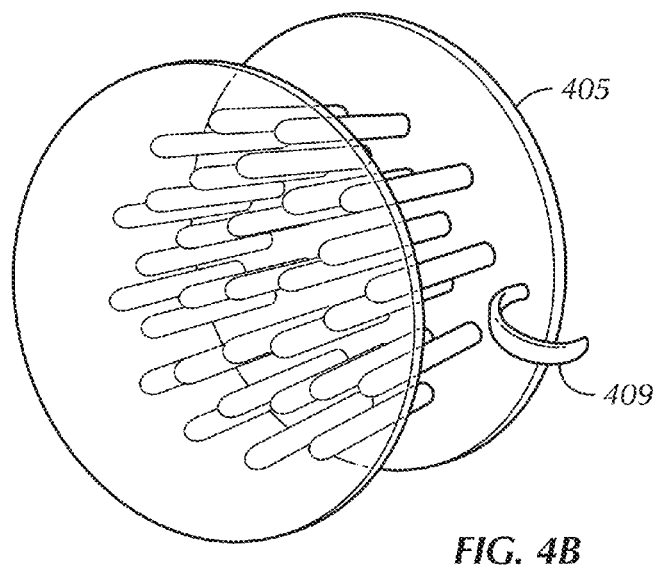

In one embodiment, the system for characterizing the dielectric response of fluids in accordance with one or more embodiments includes a plurality of separate cavities, having the same or differing resonant frequencies. In other embodiments, the length of the flow channel 409 is small relative to the typical length scale of the cavity resonant mode, as shown in FIG. 4B. In this way, one may optimize the cavity quality factor and sensitivity even in the presence of a lossy analyte. In particular, in FIG. 4B, the flow channel 409 passes through the end plate 405. The flow channel 409 then curves and returns in a direction orthogonal to the end plate 405. In FIGS. 2A, 2B and FIGS. 4A-4B the relevant cavity length scale is set by the separation between cavity end plates. In FIG. 3A, this length scale is set by the index guiding properties of the underlying dielectric waveguide. In some other embodiments, the flow channel may intersect a small fraction of the overall cavity volume.

Figure 5A:
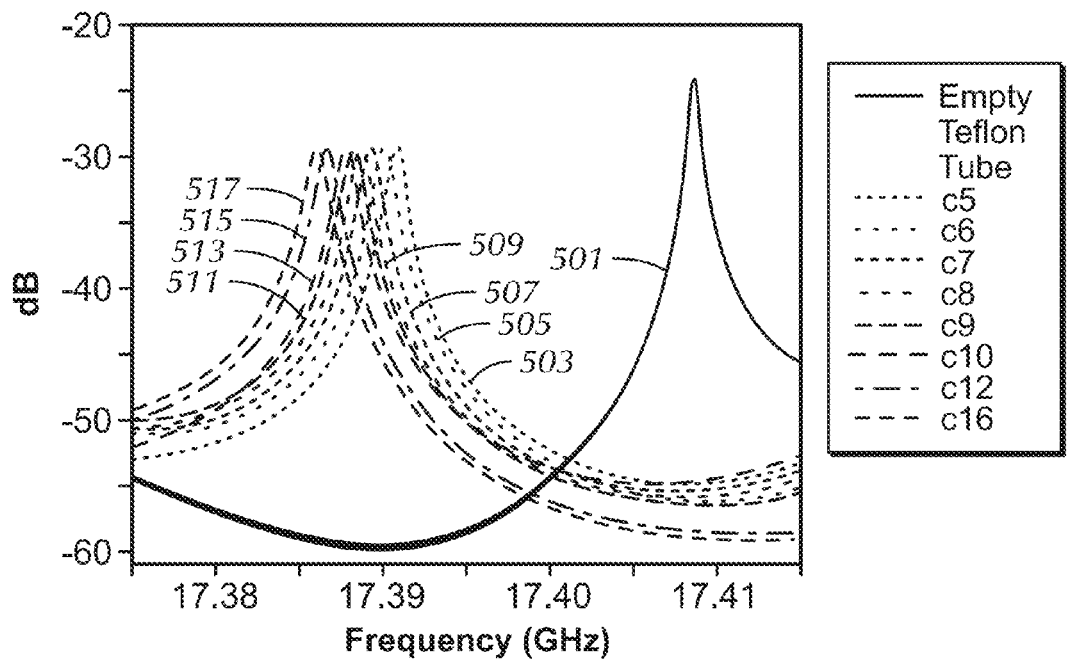
FIGS. 5A-5B show examples of test data in accordance with one or more embodiments.

FIG. 5A shows an example of the frequency response of a PBG resonant cavity measured by a signal analyzer in accordance with one or more embodiments. More specifically, referring back to FIG. 1, the data of FIG. 5A may be obtained by measuring the microwave signal that is transmitted through the cavity as a function of the frequency of the microwaves. In particular, this test data was obtained using a cavity of the type shown in FIG. 3B, having a Teflon flow line that passes through the central hole of cavity (i.e., the flow line passes through the hole that includes the largest peak of the resonant mode). One of ordinary skill will appreciate that a complimentary spectrum may also be obtained by measuring the reflected microwave power from the cavity as a function of the frequency of the microwave without departing from the scope of the present disclosure.

Curve 501 shows that the PBG resonant cavity possesses a resonant mode at 17.408 GHz when the flow line is empty. Furthermore, curve 501 also shows that the Q-factor for this particular cavity is on the order of 10,000. Curves 503-513 show additional measurements after introducing various n-alkanes into the flow line, more specifically $C_5$-$C_{10}$, $C_{12}$, and $C_{16}$ n-alkanes, respectively. As seen in the plot, the different n-alkanes result in resonant modes having different resonant frequencies and different Q-factors. Accordingly, in accordance with one or more embodiments, these properties of the resonant mode may be used to determine the type and/or composition of the fluid in the flow line.

Figure 5B:
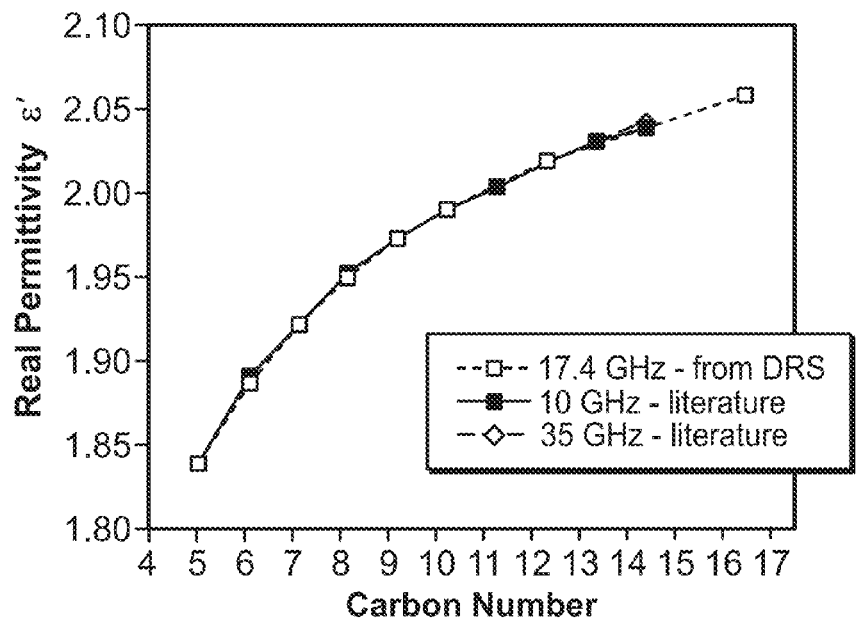
Figure 6A:
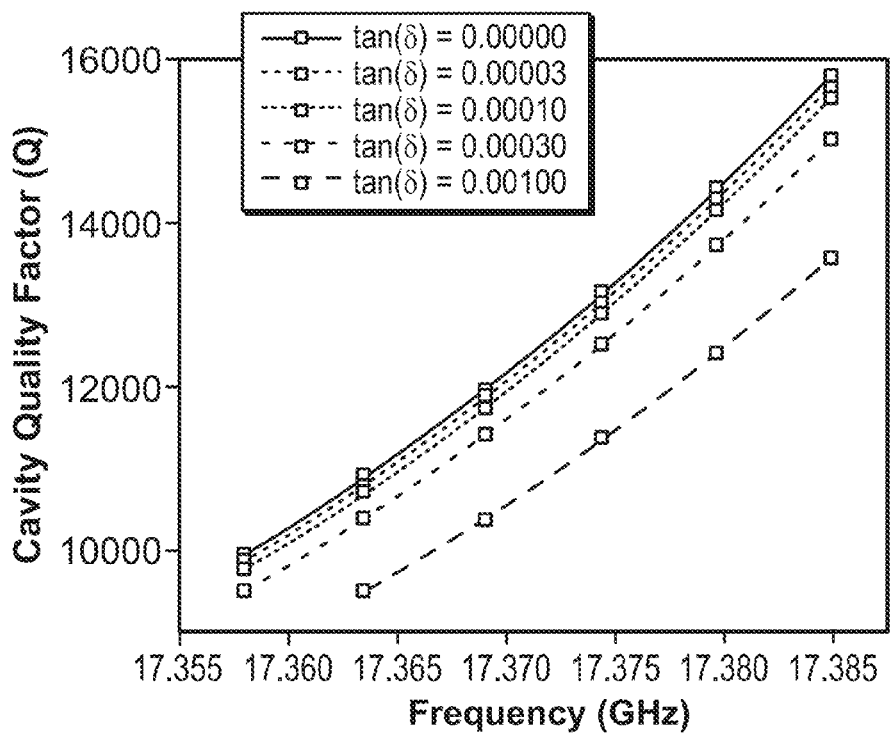
FIGS. 6A-6B shows examples of test data in accordance with one or more embodiments.
Figure 6B:
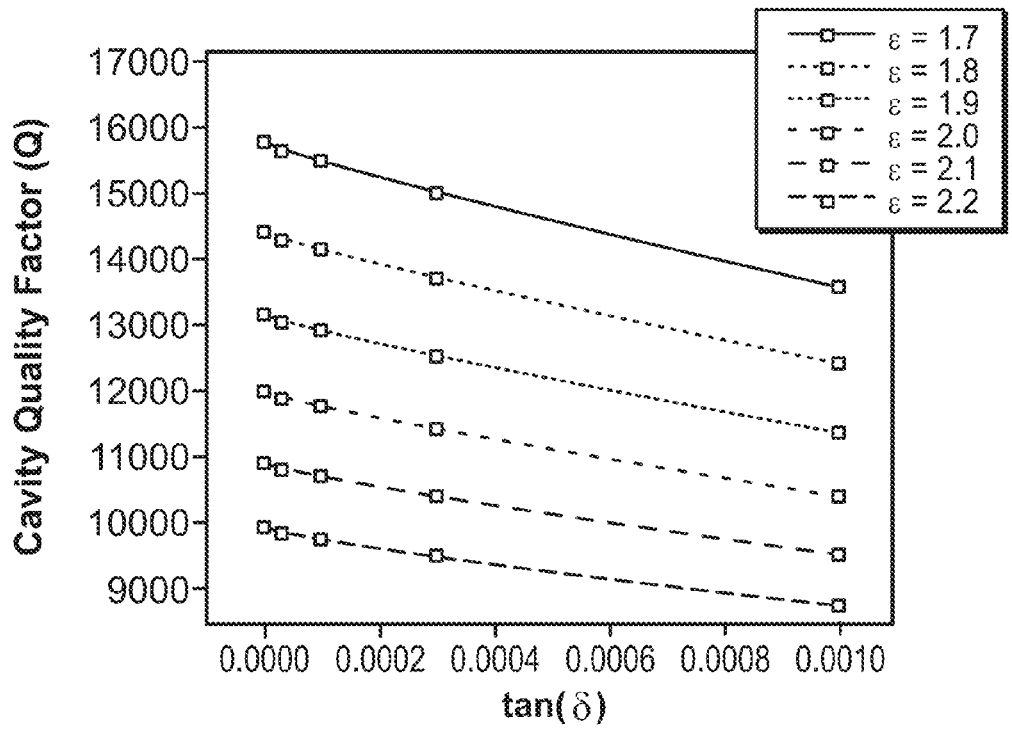

Furthermore, by numerically simulating the resonant properties of the PBG resonant cavity, the dielectric permittivity of the fluid in the flow line may be determined by numerical inversion using a model of the PBG cavity response to different analytes. FIG. 5B shows the results of such a numerical inversion indicating that the permittivities obtained by numerically inverting the measured spectra using the numerical model of the resonant cavity correspond closely with the tabulated values from the literature. Furthermore, FIG. 6A-6B illustrate one example of how the inversion may be accomplished based on an inversion grid computed using the numerical model of the cavity. More specifically, the model may be used to compute both the cavity resonant frequency as well as its Q-factor over grid computed for different values of the analyte dielectric permittivity and loss tangent, where the loss tangent is given by:

$$\tan\delta = \frac{\omega\varepsilon'' + \sigma}{\omega\varepsilon'} \approx \frac{\varepsilon''}{\varepsilon'}$$

and the complex permittivity is given by $\in = \in' + i\in''$. In this example, a PTFE tube is used for the fill line ($\in$=2.05, $\tan(\delta)$=2E−4), where the tube accounts for approximately 50% of sample volume.

Figure 7:
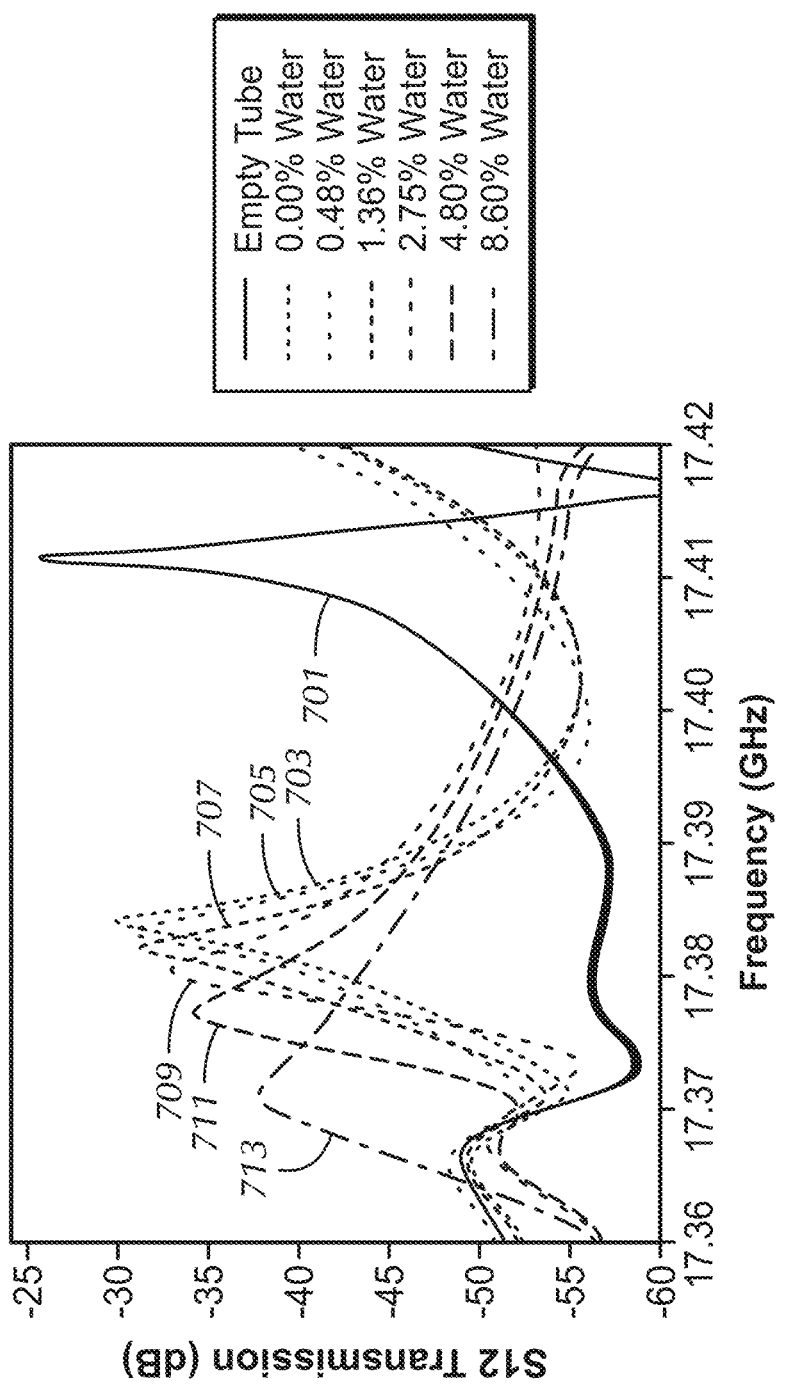
FIG. 7 shows an example of test data in accordance with one or more embodiments.
Figure 8A:
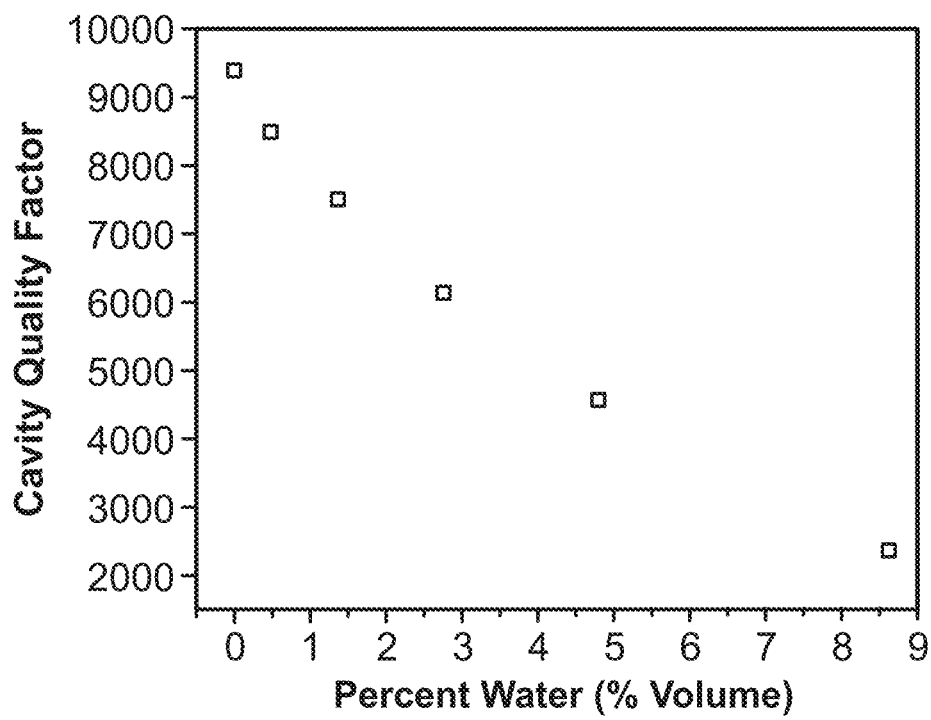
FIGS. 8A-B show examples of test data in accordance with one or more embodiments.
Figure 8B:
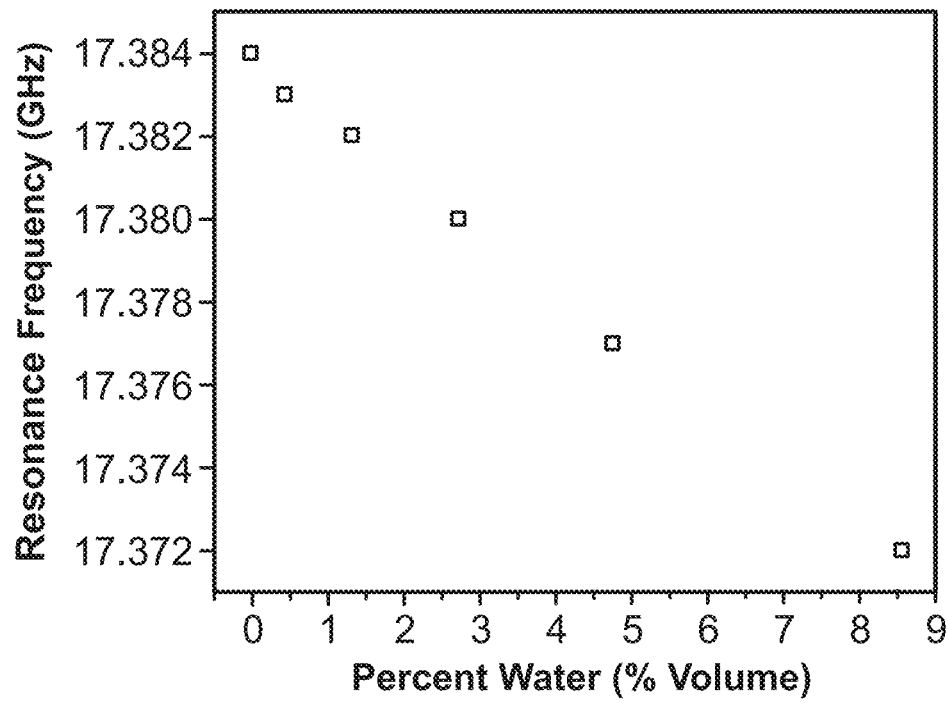

FIG. 7 shows additional test data using a PBG resonant cavity in accordance with one or more embodiments. More specifically, FIG. 7 shows examples of test data measured using various crude oil and water mixtures. Curve 701 shows the results for an empty flow line while curves 703-713 show the cavity response when a water fraction of 0.00%, 0.48%, 1.36%, 2.75%, 4.80% and 8.60%, respectively, was emulsified and added to the crude. FIGS. 8A-8B show the measured Q-factors and resonance frequencies plotted against the water fractions to illustrate the correlation that may be used to invert measured resonant frequencies and/or Q-factor data to obtain the water fraction in the mixture. Such a method may be reliably used when the dielectric properties of the crude oil type to be encountered in the field are known in advance such that calibration curves FIGS. 8A-8B may be generated in advance during a calibration procedure. More generally, the method may be reliably used for any mixture of fluids when the types of fluids to be encountered are known in advance such that the calibration curves similar to those shown in FIGS. 8A-8B may be generated in advance during a calibration procedure.

Figure 9A:
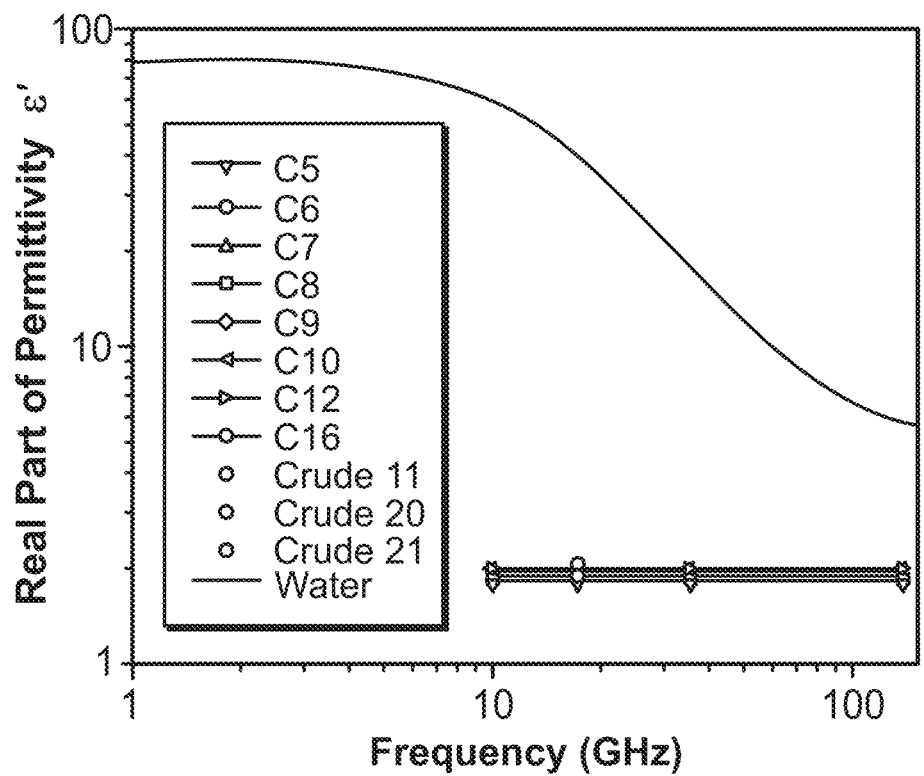
FIGS. 9A-B show examples of test data in accordance with one or more embodiments.
Figure 9B:
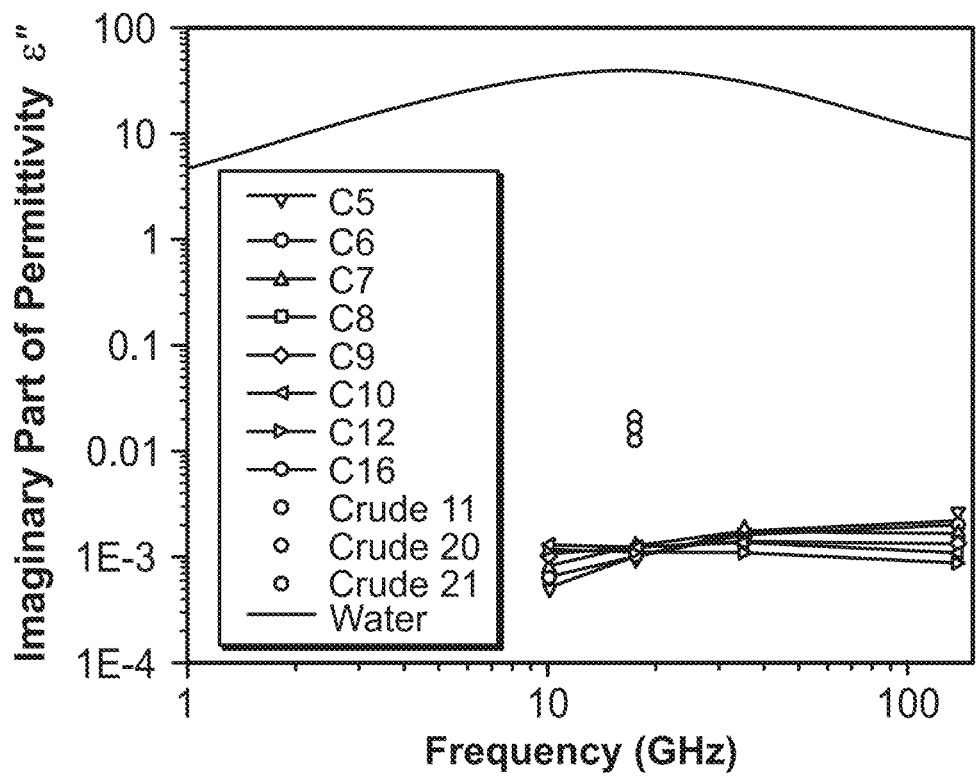

However, in the case of water and oil, the water fraction and water conductivity may be determined without prior knowledge of the oil type by using a multi-frequency measurement method in accordance with one or more embodiments. The complex permittivity of many types of crudes is frequency independent (i.e., $\in'$ and $\in''$ of oil and gas have negligible frequency dispersion), while the complex permittivity of water and/or brine is strongly frequency dependent (i.e., both $\in'$ and $\in''$ of water and/or brine have strong frequency dispersion). In addition, compared to the value of the imaginary part of the permittivity of water, the imaginary part of the permittivity of crude is negligible. These points are summarized in the plots shown in FIGS. 9A-9B.

Assuming a mixing model, e.g., Bruggeman, Maxwell Garnett, etc., permittivity of the oil $\in_{oil}$ and permittivity of the brine $\in_{brine}$ may be combined to give the resulting permittivity $\in(\omega)$ of the mixture. For example, using a simple mixing model, such as one defined by the following relation $$\in(\omega) = (1-\Phi)\in_{oil} + \Phi\in_{brine}$$

where $\Phi$ is the brine-volume fraction and with the assumptions that $\in_{oil}$ is a constant over frequency and $$\varepsilon_{brine} = \varepsilon_{water} + i\frac{\sigma}{\omega\varepsilon_0}$$

the sum and difference of the real and imaginary parts of the measured permittivity $\in(\omega)$ are $$Re[\in(\omega_1) - \in(\omega_2)] \sim \Phi\Delta Re(\in_{water})$$

$$Im[\in(\omega_1) - \in(\omega_2)] \sim \Phi\Delta Im(\in_{water}) + (1/\omega_1 - 1/\omega_2)\sigma/\in_0$$

where $\in_0$ is the permittivity of free space, $\sigma$ is the water conductivity and $\omega_1$ and $\omega_2$ are the frequencies at which the complex permittivity $\in(\omega)$ of the fluid is measured, and $\Delta Re(\in)$ and $\Delta Im(\in)$ are non zero and correspond to the change in water/brine permittivity across the measurement interval from $\omega_1$ to $\omega_2$. For example, in this case, a PBG resonant cavity with two resonant modes having different frequencies may be used or two different PBG resonant cavities may be used each placed along the flow line and each PBG resonant cavity having a different resonant mode with a different resonant frequency. Because $\in_{water}$ is known, for a given temperature and pressure, both $\Phi$ and $\sigma$ may be determined without the knowledge of the oil permittivity. Furthermore, once the $\Phi$ and $\sigma$ are determined, $\in_{oil}$ may be determined using the single frequency measurements and the relation.

With different mixing models, analogous expressions with other algebraic forms can be obtained and/or empirically derived formulas can be used to determine the water fraction. Examples of other mixing models include Bruggeman, Maxwell Garnett, power laws, and other parametric expressions. The method for determining water fraction described above can be applied to determine the volume fraction of any one fluid component that has a strong frequency dependent permittivity function, such as the generalized Debye permittivity function of common liquids containing polar molecules. Such common liquids may include water, alcohols, and solvents (e.g., ethanol, methanol, acetone, dimethyl-sulfoxide, nitromethane, etc.).

Thus, the above method for the characterization of the dielectric response of fluids may be used to determine 1) the water volume fraction; 2) the water conductivity (salinity); and 3) the oil permittivity using a two frequency measurement that employs PBG resonant cavities. Advantageously, all three quantities above may be determined without prior knowledge of any one of them. In contrast, a single frequency measurement uses prior knowledge of at least one of the quantities. For example, as described above, a single frequency (i.e., single resonant frequency) measurement produces two quantities, the cavity mode resonant frequency and the cavity mode Q-factor. As described above, these two quantities may be numerically inverted using a model of the cavity to obtain the real and imaginary parts of the permittivity of the fluid $\in'$ and $\in''$, respectively. One of ordinary skill will appreciate that using the geometry of the cavity, numerical techniques (e.g., like those available in commercial mode-solving software) $\in'$ may be determined from the mode resonant frequency while $\in''$ may be determined from the Q-factor of the mode. One of ordinary skill will also appreciate that for some cavity designs closed form solutions may be available, thus precluding the need for a complete numerical simulation of the cavity. In addition, while the above example uses two separate frequency measurements, the above method may be used with three or more measurements at three or more different frequencies without departing from the scope of the present disclosure. For example, three frequency measurements make for a better constrained system while many measurements allows for the fitting of the measured data to response shapes having various functional forms. One of ordinary skill will appreciate that in many cases, iterative solution algorithms may be employed in cases where the overall cavity response to the complex permittivity of the analyte differs from the simple expressions given above.

Figure 10:
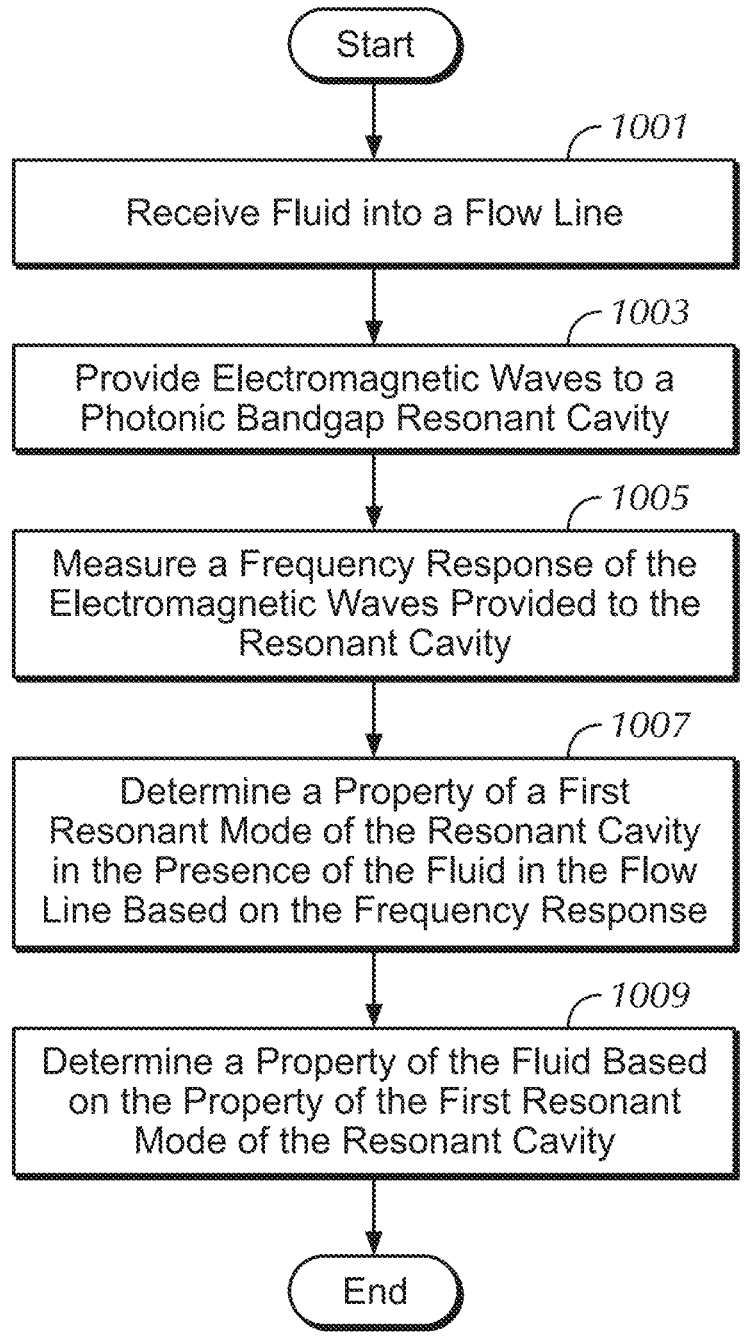
FIG. 10 shows an example method in accordance with one or more embodiments.

FIG. 10 illustrates an example method in accordance with one or more embodiments. Specifically, FIG. 10 illustrates a method for the characterization of the dielectric response of fluids using a PBG resonant cavity in accordance with one or more embodiments. In step 1001, a fluid to be tested is received into a flow line of the system. For example, the system may be a system as described above in reference to FIG. 1.

In accordance with one or more embodiments, the flow line is located within or near to a PBG resonant cavity possessing at least one resonant mode, as described above in reference to FIGS. 2-4. For example, the flow line may pass through a defect region in the PBG resonant cavity as shown in FIGS. 2A, 2B, and FIG. 4. In another example, the flow line may pass near, or adjacent to, the spatially localized resonant mode of the PBG resonant cavity, for example at a distance z away from the center of the localized resonant mode, as shown in FIG. 3C. One of ordinary skill will appreciate that while the example of microwave PBG cavities are detailed above, the method may deploy any type/geometry of PBG resonant cavity and, thus, can operate at any frequency in the electromagnetic spectrum.

In step 1003, electromagnetic waves are provided to the PBG resonant cavity. As described above in reference to FIG. 1, the electromagnetic waves may be generated by a signal generator capable of generating electromagnetic waves across a range of frequencies. Furthermore, the frequency of the electromagnetic waves may be varied, or swept from a beginning frequency to an ending frequency. For example, as shown in FIGS. 5 and 7, the frequency may be swept from 17.36 GHz-17.42 GHz. One of ordinary skill will appreciate that the relevant frequency range is determined by the nature of the fluid under investigation, as well and the design of the PBG resonant cavity and is limited only by the capabilities of the signal generator.

In step 1005, the frequency response of the electromagnetic waves provided to the resonant cavity is measured. In accordance with one or more embodiments, the frequency response includes measuring, as a function of frequency, the electromagnetic waves that are reflected and/or transmitted from the PBG resonant cavity. As shown, e.g., in FIG. 5, the frequency response includes a resonance line shape due to the presence of the resonant mode of the PBG resonant cavity. Thus, at step 1007, the properties of the resonant mode, e.g., the resonant frequency and the Q-factor may be determined by the location of the peak and width of the resonance line shape of the measured frequency response.

In step 1009, one or more properties of the fluid under test are determined based upon the properties of the measured frequency response, e.g., by using the determined resonant frequency and Q-factor, as described above in reference to FIGS. 5-9. For example, both the real and imaginary part of the complex permittivity of the fluid may be computed using the measured resonance frequency and Q-factor in conjunction with a numerical model of the resonant cavity. In another example, a property of the fluid may be determined directly from the resonant frequency and Q-factor using a previously determined calibration, e.g., like that shown in FIG. 8A-8B. As discussed above, numerous properties of the fluid may be determined, including, water fraction, carbon number, or the like.

Figure 11:
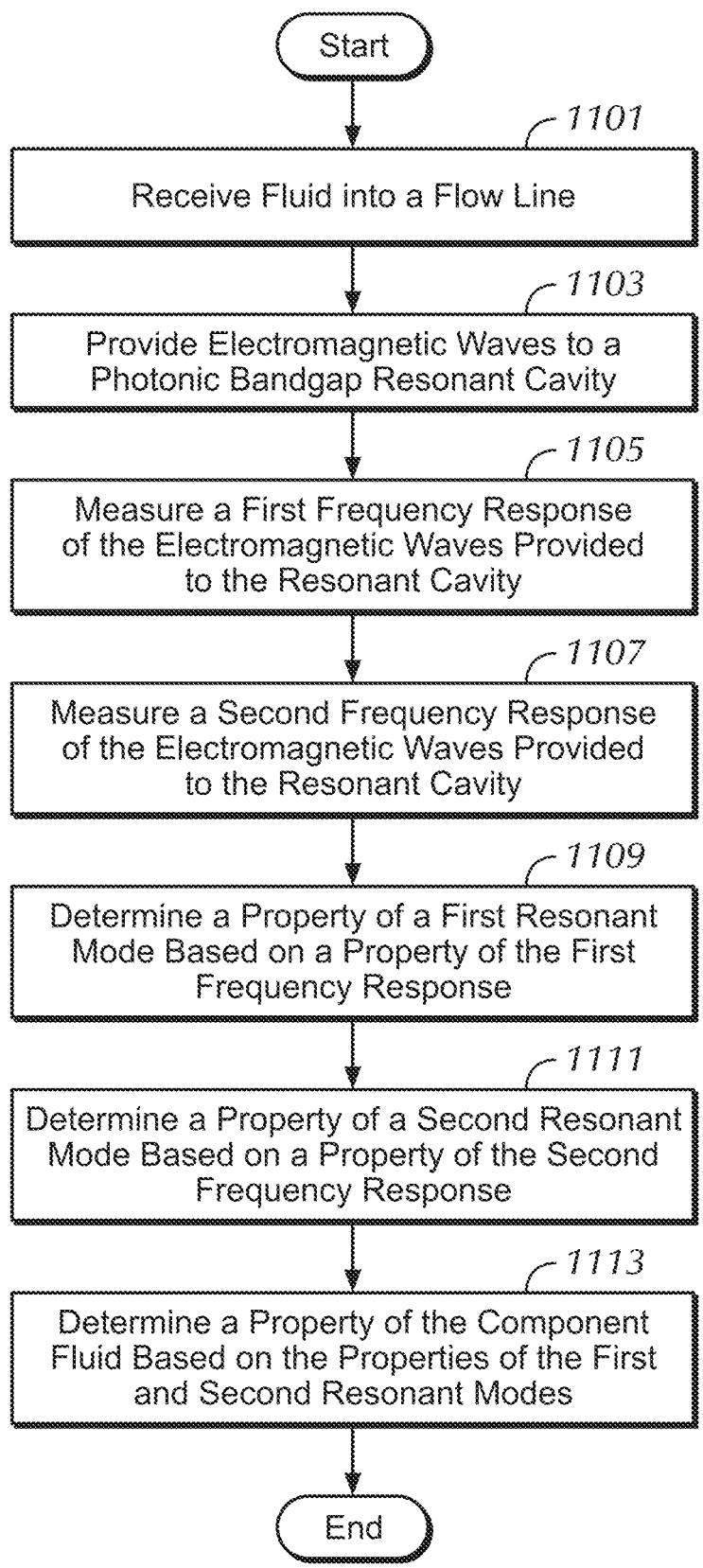
FIG. 11 shows an example method in accordance with one or more embodiments.

FIG. 11 illustrates an example method in accordance with one or more embodiments. Specifically, FIG. 11 illustrates a method for the characterization of the dielectric response of fluids using a PBG resonant cavity in accordance with one or more embodiments. For example, the method of FIG. 11 may be used to determine the water fraction, salinity, and base oil permittivity of a fluid without prior knowledge of any one of the water fraction, salinity, and base oil permittivity. The method proceeds similarly to the single resonant frequency measurement method described above in reference to FIG. 10. However, FIG. 11 employs the measurement of at least two different resonant frequencies.

In step 1101 a fluid to be tested is received into a flow line of the system. For example, the system may be a system as described above in reference to FIG. 1. Furthermore, the system may be deployed as a stand-alone analytical instrument, e.g., as a lab-based analytical instrument or as ruggedized unit for field work, or as part of a downhole logging tool for characterizing downhole fluids. For example, fluids of interest may include borehole fluids such as drilling muds, production fluids, filtrate fluids, fluids sampled directly from the underground formation and/or fluids injected into an underground formation, casing or pipeline. However, the dielectric response of any fluid may be characterized without departing from the scope of the present disclosure.

Figure 12A:
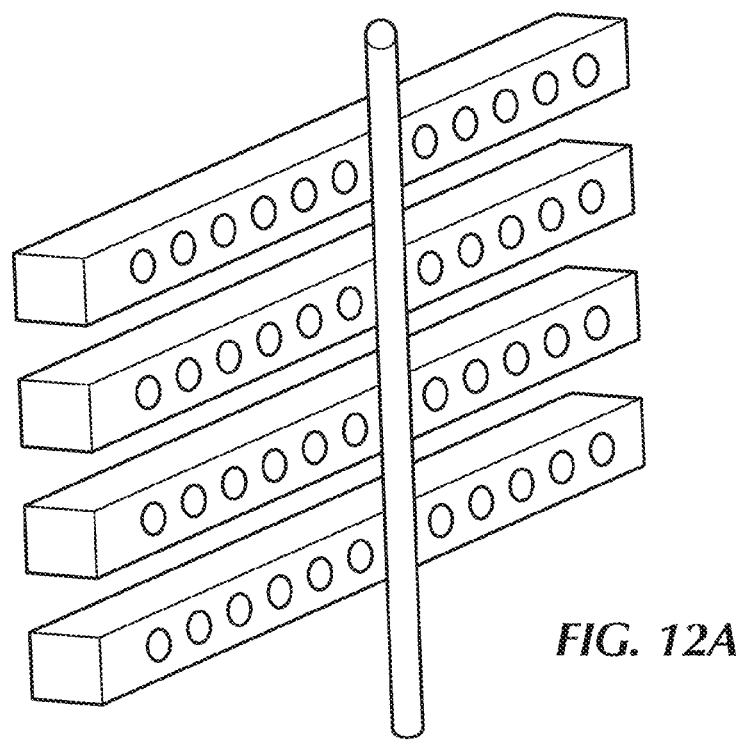
FIGS. 12A-12B show examples of photonic bandgap resonant cavities in accordance with one or more embodiments.
Figure 12B:
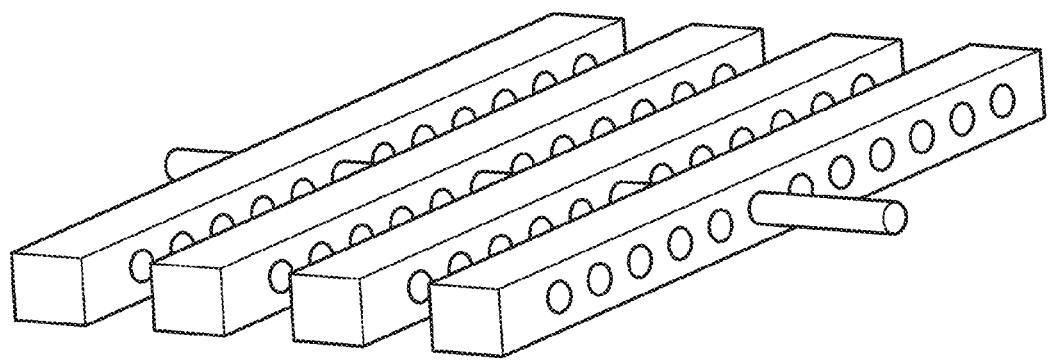

In accordance with one or more embodiments, the flow line is disposed within or proximate to a PBG resonant cavity possessing at least two resonant modes. For example, the multi-mode resonant cavity may be any one of the resonant cavities shown and described above in reference to FIGS. 2-4. In other embodiments, the multi-frequency measurement system my comprise of a system of independent PBG cavities as shown in FIG. 12A-12B for the cavity of FIG. 3. In this arrangement, each resonant cavity may possess a different resonant frequency so as to probe the dielectric response of the fluid at several distinct frequencies. In some other embodiments, any combination of resonant cavities, including multi-mode cavities may be employed. In what follows, a two frequency measurement will be described but any number of measurements may be used without departing from the scope of the present disclosure.

Similarly to that described above in reference to FIG. 10, the flow line in a multi-frequency system may pass through a defect region in the PBG resonant cavity as shown in FIG. 12B or the flow line may pass adjacent to the cavities, as shown in FIG. 12A. One of ordinary skill will appreciate that while the example of microwave PBG cavities are detailed above, the method may deploy any type/geometry of PBG resonant cavity and thus can operate at any frequency in the electromagnetic spectrum.

In step 1103, electromagnetic waves are provided to the PBG resonant cavity. As described above in reference to FIG. 1, the electromagnetic waves may be generated by a signal generator capable of generating electromagnetic waves across a range of frequencies. Furthermore, the frequency of the electromagnetic waves may be varied, or swept from a beginning frequency to an ending frequency.

In step 1105, a first frequency response of the electromagnetic waves provided to the resonant cavity is measured. In accordance with one or more embodiments, the first frequency response includes measuring, as a function of frequency, the electromagnetic waves that are reflected and/or transmitted from the PBG resonant cavity.

In step 1107, a second frequency response of the electromagnetic waves provided to the resonant cavity is measured. In accordance with one or more embodiments, the second frequency response includes measuring, as a function of frequency, the electromagnetic waves that are reflected and/or transmitted from the PBG resonant cavity. As shown, e.g., in FIG. 5, the frequency response includes a resonance line shape due to the presence of the second resonant mode of the resonant cavity.

As described above, the first and second resonant modes possess different resonant frequencies. Accordingly, the electromagnetic waves provided to the resonant cavity may include frequencies that are near the resonant frequencies of the resonant modes.

At steps 1109 and 1111, the properties of the first and second resonant modes, e.g., the resonant frequencies and the Q-factors may be determined by the location of the peaks and widths of the resonance line shapes of the measured frequency responses. At step 1113, a property of the fluid, or a component of the fluid may be determined based upon the measured resonant frequencies and Q-factors, as described above in reference to FIGS. 8-11.

Figure 13A:
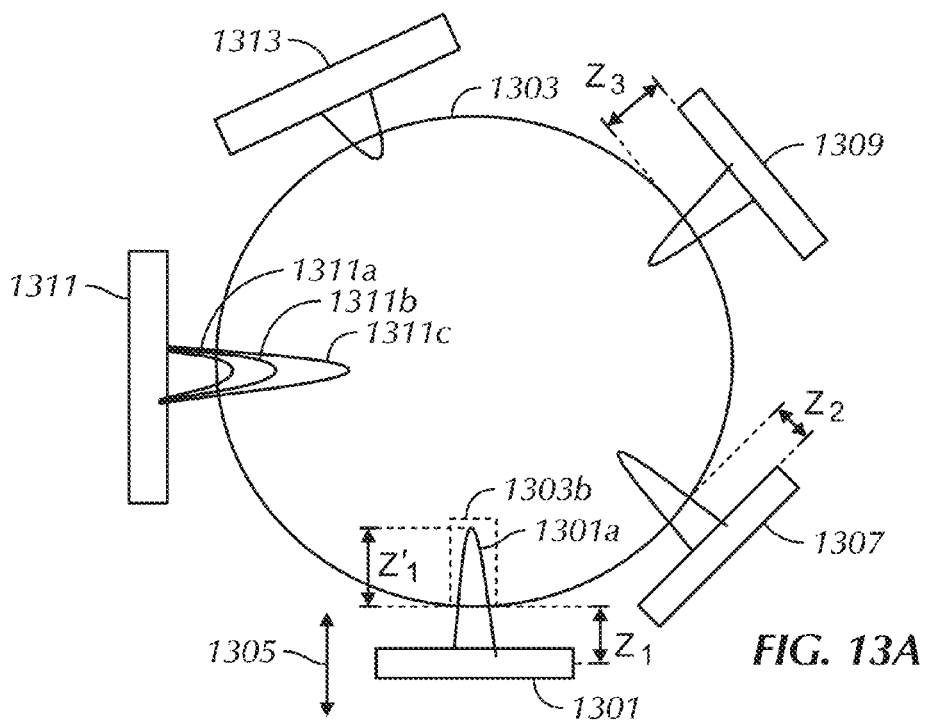
FIGS. 13A-13C show examples of systems for characterizing the dielectric response of fluids in accordance with one or more embodiments.
Figure 13B:
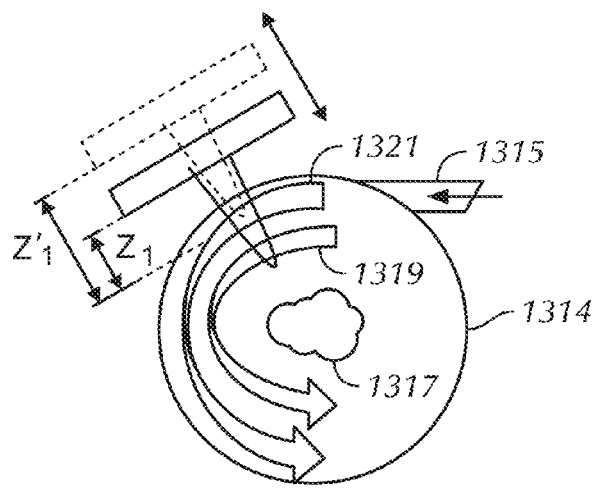

FIGS. 13A-13B show an apparatus for the characterization of the dielectric response of fluids in accordance with one or more embodiments. More specifically, FIG. 13A shows an example of a resonant cavity 1301 located adjacent to a flow line 1303, or fluid vessel 1303, shown in cross-section. In accordance with one or more embodiments, the vessel 1303 may include various types of fluids or mixtures of fluids under test, e.g., production fluids, drilling muds, borehole fluids generally, or the like. In accordance with one or more embodiments, a resonant cavity 1301 is mounted adjacent to the vessel 1303 at a distance $z_1$ away from the outer surface of the vessel 1303. Accordingly, the spatially localized resonant mode 1301a of the resonant cavity 1301 extends a distance $z_1'$ into the fluid vessel 1303 thereby allowing the characterization of the fluid in a distinct spatial region 1303b inside the vessel. The distinct spatial region 1303b generally includes the volume of fluid that overlaps the spatially localized resonant mode 1301a. In accordance with one or more embodiments, the distance $z_1$ may be variable, e.g., by translating the resonant cavity 1301 along a generally radial direction 1305. Alternatively, or in combination with a movable resonant cavity, several resonant cavities 1301, 1307, and 1309 may be mounted around the circumference or length of the vessel, where each resonant cavity is mounted at a different distance from the vessel wall, indicated in the figure as distances $z_1$, $z_2$ and $z_3$, respectively. The distances at which the multiple cavities are mounted away from the vessel wall may be fixed or may be variable without departing from the scope of the present disclosure. In another embodiment, a cavity 1311 may be designed having several different localized spatial modes, e.g. modes 1311a-1311c. In accordance with one or more embodiments, the localized spatial modes of the cavity 1311 may each extend a different distance into the vessel so as so sample the fluid within the vessel at different distances. Furthermore, several different cavities, e.g., cavities 1301, 1307, and 1313, each cavity having a different sized localized spatial mode may be arranged around the surface of the vessel 1303. While FIG. 13A shows a vessel with multiple cavity arrangements employed simultaneously, this is done merely for the sake of compactness. Any arrangement or combination of arrangements may be employed without departing from the scope of the present disclosure.

FIG. 13B shows an example of one type of vessel that may be employed in the apparatus for the characterization of the dielectric response of fluids in accordance with one or more embodiments. More specifically, FIG. 13B shows an example of a swirl flow separator 1314 used to separate the phases of a multi-phase fluid in accordance with one or more embodiments. For example, the fluid may enter the separator 1314 by way of inlet 1315 and be forced by the separator into a swirling motion that, as a result of the effect of inertial forces, serves to spatially separate, in the radial direction, the constituent phases of the multi-phase fluid, into e.g., gas phase 1317, oil phase 1319, and water phase 1321. As described above, in reference to FIG. 13A, a resonant cavity may be mounted adjacent to the vessel so as to enable to sampling of fluid internal to the vessel at several different depths within the vessel wall.

Shown in FIG. 13B is an arrangement showing a single cavity mounted at a variable distance $z_1$ from the surface of the vessel. Alternatively, or in combination with this arrangement, any of the arrangements shown in FIG. 13A may be used.

Figure 13C:
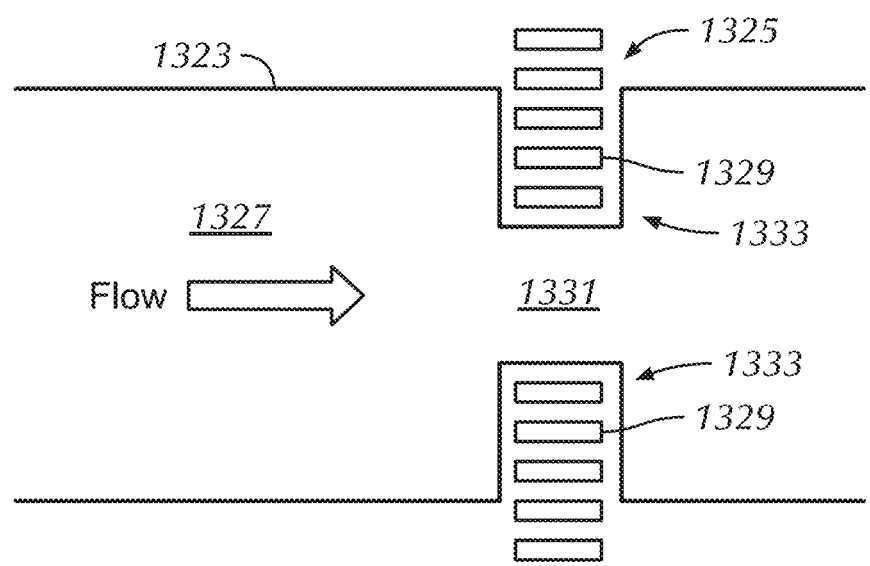

Advantageously, one or more cavities may be employed as shown in, e.g., FIGS. 13A-13B to implement a multi-phase flow meter, or any other arrangement shown above may also be implemented in a flow meter configuration. One such configuration is shown in FIG. 13C. For example, in a flow meter configuration, a known time dependent perturbation, or modulation, of the complex permittivity of the fluid entering the vessel 1323, e.g., a pipeline may be employed at a location upstream from the flow meter 1325. The perturbation, or modulation may be a single pulse introduced into the fluid 1327 at any known time, or may be introduced at a regular periodic rate, with a known frequency and phase. By determining the time elapsed between initiation of the perturbation and detection of the perturbation, the fluid velocity may be determined by dividing the distance between the initiation point and the detection point by the elapsed time. Accordingly, when the volume of the vessel is known, a volumetric flow quantity (e.g., volume/time) may be determined. Likewise, mass flow may also be determined if the density of the fluid is known. The example shown in FIG. 13C employs a resonant cavity 1329 formed from two Bragg mirrors as described above. Accordingly, the flow passage 1331 forms the interior of the resonant cavity 1329 and contains a spatially localized mode that may be affected by the dielectric properties of the fluid 1327, as described above. In accordance with one or more embodiments, the vessel 1323 may include windows 1333 that are transparent to the electromagnetic wave being used (e.g., in the microwave part of the spectrum).

In accordance with one or more embodiments, the perturbation, or modulation may be accomplished any number of different ways without departing from the scope of the present disclosure. For example, a sample of tracer particles may be injected into the fluid at an upstream location and the presence of these particles may be detected at some time later at a downstream location. In accordance with one or more embodiments, the tracer particles may be particles that modify the complex permittivity of the fluid, e.g., $TiO_2$ particles, salts, nanoparticles having a predesigned dielectric response, or the like. The introduction of these particles serves to change the complex permittivity (real part and/or imaginary part) of the fluid and accordingly, this change, may be detected by an instrument that employs a PBG resonant cavity as described herein. Alternatively, the density (and, thus, indirectly the complex permittivity) of the fluid may be modulated by introducing a pressure wave into the fluid at a location that is upstream to flow meter. For example, a mechanical piston or the like, may introduce one or more compressional pulses into the fluid at the upstream location and this pulse may be detected at the downstream location as a modulation, or perturbation in the complex permittivity of the fluid. Accordingly, if the velocity of the compression wave and distance between the piston and the detector are known, the fluid velocity may be determined. One of ordinary skill having the benefit of this disclosure will appreciate that flow metering in accordance with one or more embodiments of the invention is not limited to the multi-phase flow metering example described above, but may be employed in any fluid without departing from the scope of the present disclosure.

Figure 14:
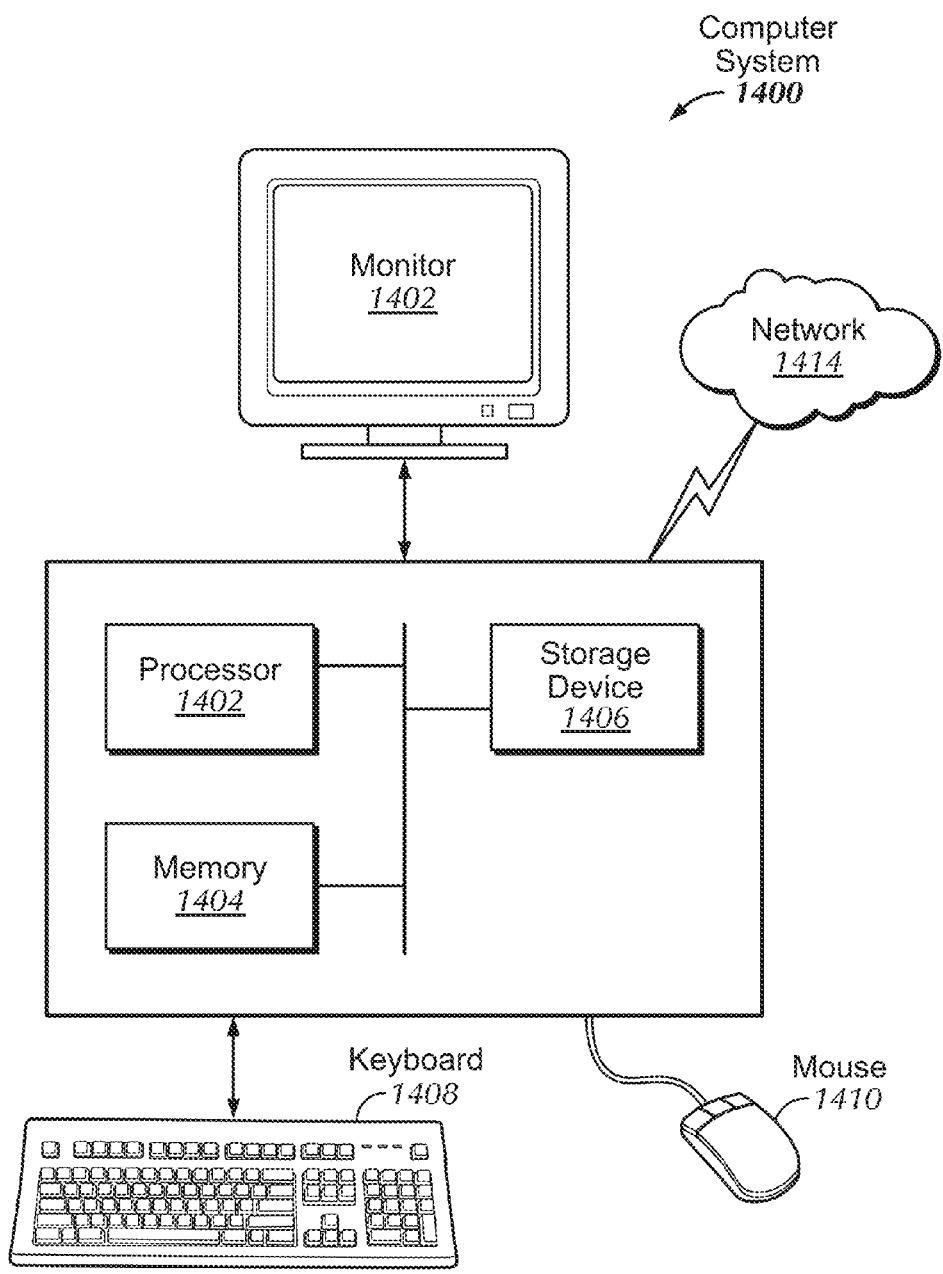
FIG. 14 shows an example of a computer system to be employed in accordance with one or more embodiments.

In accordance with one or more embodiments, portions of the systems and methods disclosed herein may include, or be implemented on, virtually any type of computer regardless of the platform being used. For instance, as shown in FIG. 14, a computer system 1400 includes one or more processor(s) 1402 such as an integrated circuit, a central processing unit (CPU) or other hardware processor, associated memory 1404 (e.g., random access memory (RAM), cache memory, flash memory, etc.), a storage device 1406 (e.g., a hard disk, an optical drive such as a compact disk drive or digital video disk (DVD) drive, a flash memory stick, etc.), and numerous other elements and functionalities typical of today's computers (not shown). The computer 1400 may also include input means, such as a keyboard 1408, a mouse 1410, or a microphone (not shown). Further, the computer 1400 may include output means, such as a monitor 1412 (e.g., a liquid crystal display LCD, a plasma display, or cathode ray tube (CRT) monitor). The computer system 1400 may be connected to a network 1414 (e.g., a local area network (LAN), a wide area network (WAN) such as the Internet, or any other similar type of network) via a network interface connection (not shown). Those skilled in the art will appreciate that many different types of computer systems exist (e.g., desktop computer, a laptop computer, a personal media device, a mobile device, such as a cell phone or personal digital assistant, or any other computing system capable of executing computer readable instructions), and the aforementioned input and output means may take other forms, now known or later developed. Generally speaking, the computer system 1400 includes at least the minimal processing, input, and/or output means necessary to practice one or more embodiments.

Further, those skilled in the art will appreciate that one or more elements of the aforementioned computer system 1400 may be located within a downhole logging tool or may be located at a remote location and connected to the other elements over a network. Further, one or more embodiments may be implemented on a distributed system having a plurality of nodes, where each portion of the implementation may be located on a different node within the distributed system. In one or more embodiments, the node corresponds to a computer system. Alternatively, the node may correspond to a processor with associated physical memory that may be located at a downhole and/or an uphole location. The node may alternatively correspond to a processor with shared memory and/or resources. Further, software instructions to perform one or more embodiments may be stored on a computer readable medium such as a compact disc (CD), a diskette, a tape, or any other computer readable storage device.

Figure 15:
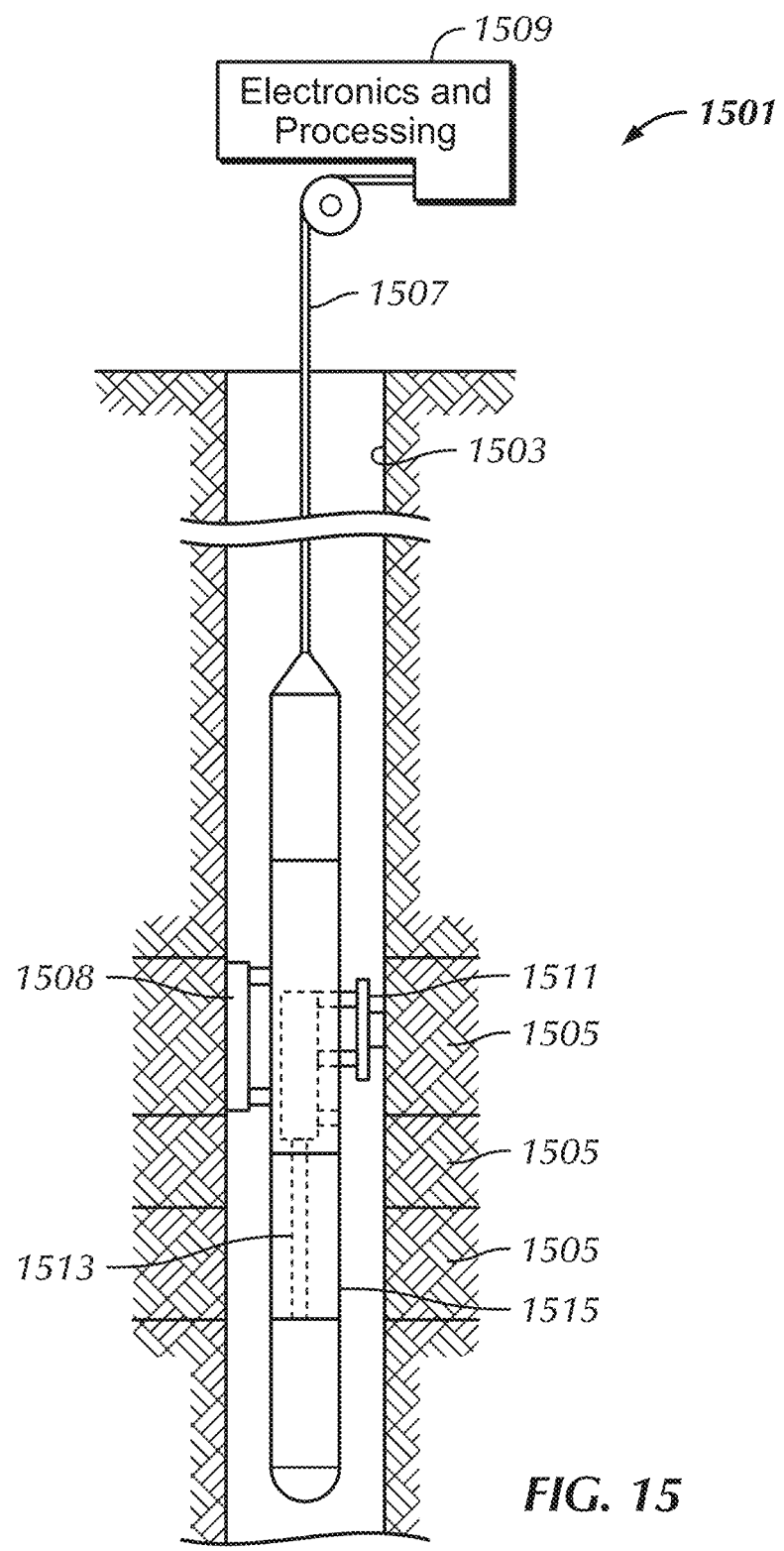
FIG. 15 shows an example of a borehole tool in accordance with one or more embodiments.

Furthermore, in accordance with one or more embodiments, the system may be deployed as a stand-alone analytical instrument, e.g., as a lab-based analytical instrument or as ruggedized unit for field work, or as part of a downhole logging tool for characterizing downhole fluids, such as a wireline tool. For example, FIG. 15 shows a wireline tool in accordance with one or more embodiments. The wireline tool 1501 is typically lowered into a borehole 1503 that traverses a formation 1505 using a cable 1507. The wireline tool 1501 is lowered down into the borehole 1503 and makes a number of measurements of the adjacent formation at a plurality of sampling locations along the borehole. The data from these measurements is communicated through the cable 1507 to surface equipment 1509, which may include a computer system for storing and processing the data obtained by the wireline tool (e.g., a truck or a cabin on an off-shore platform). The wireline tool 1501 may include a selectively extendable fluid admitting assembly 1511 (e.g., probe). This assembly 1511 extends into the formation 1505 and withdraws formation fluid from the formation (e.g., samples the formation). The wireline tool 1501 may also include a selectively extendable tool anchoring member 1508 that is arranged to press the probe 1511 assembly against the formation 1505. The fluid flows through the assembly 1511 and into a flow line 1513 within a housing of the tool. A pump (not shown) can be used to withdraw the formation fluid from the formation 1505 and pass the fluid through the flow line 1513. In accordance with one or more embodiments, the system described herein may be deployed as an additional module 1515 through which the flow line 1513 runs. Accordingly, the system can be used to analyze fluids within the flow line 1513 or other flow lines (not shown) within the wireline tool.

The system described herein is not limited to use with wireline tools or systems. For example, the embodiments described herein can also be used with any suitable means of conveyance, such coiled tubing. Furthermore, various embodiments of the present disclosure may also be applied in logging-while-drilling (LWD) operations, sampling-while-drilling operations, measuring-while-drilling operations, well production operations or any other operation where sampling of fluid is performed. Fluids of interest may include borehole fluids such as drilling muds, production fluids, filtrate fluids, fluids sampled directly from the underground formation and/or fluids injected into an underground formation, casing or pipeline. However, the dielectric response any fluid may be characterized without departing from the scope of the present disclosure.

The systems and methods disclosed herein generally relate to a method for the characterization of the dielectric response of fluids. It will be appreciated that the same systems and methods may be used for performing subsurface fluid analysis in fields such as oilfield, mining, water retrieval, or in any field where fluid characterization is desired. For example, in an oilfield application, the system and methods disclosed herein may take the form of, or be implemented within, a downhole fluid sampling tool for determining the purity of a fluid sample, e.g., for monitoring borehole mud contamination. In other downhole examples, the fluid sample tool may be employed in a production line for monitoring of production fluids, e.g., as a function of position along the borehole. In other embodiments, the system and methods may be deployed uphole as an analytical instrument for monitoring any type of fluid in any type of vessel, e.g., as a multiphase flow meter or as a monitor for monitoring drilling mud composition. The systems and methods may also be deployed in subsea applications, e.g., in sub-sea pipeline applications for determining fluid properties. For example the system may be deployed on a subsea pipeline for determining early water fraction breakout, a significant problem that may lead to hydrate formation. In addition, the system and methods disclosed herein may be deployed to detect the injection of remedial or hydrate prevention agents such as methanol, glycol, or the like. Other pipeline applications include, e.g., gas-volume fraction determinations. More generally, the multi-frequency systems and methods disclosed herein advantageously allow for the measurement of oil, gas and/or brine volume fractions, in addition to the volume fractions of intervention fluids such as methanol, e.g., in pipelines, in borehole tools, and in surface installations. However, the system and methods disclosed herein are not limited to the above-mentioned applications and these applications are included herein merely as a subset of examples. Furthermore, portions of the systems and methods may be implemented as software, hardware, firmware, or combinations thereof.

Although only a few example embodiments have been described in detail above, those skilled in the art will readily appreciate that many modifications are possible in the example embodiments without materially departing from the apparatus and method for the characterization of the dielectric response of fluids. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

The invention claimed is:

1. A system for characterizing a dielectric response of a borehole fluid, the system comprising:
    a wave generator configured to generate electromagnetic waves in a microwave frequency range of 300 MHz to 300 GHz;
    a first photonic bandgap (PBG) microwave resonant cavity electromagnetically coupled to the wave generator such that the resonant cavity is configured to receive the electromagnetic waves, the resonant cavity comprising a first resonant frequency;
    a flow line electromagnetically coupled to the resonant cavity and configured to convey the borehole fluid so that the borehole fluid within the flow line affects a frequency response of the resonant cavity in response to the electromagnetic waves; and
    a signal analyzer configured to measure the frequency response of the resonant cavity.

2. The system of claim 1, wherein the resonant cavity comprises a periodic arrangement of materials that generates a resonant mode and the flow line passes in proximity to the resonant mode.

3. The system of claim 2, wherein the periodic arrangement comprises a plurality of holes in a base material of the resonant cavity.

4. The system of claim 2, wherein the periodic arrangement comprises a plurality of rods extending from a base material of the resonant cavity.

5. The system of claim 4, wherein the plurality of rods are disposed within a dielectric material.

6. The system of claim 2, wherein the periodic arrangement comprises a plurality of concentric layers and the layers are concentric about the flow line.

7. The system of claim 2, wherein the periodic arrangement comprises a plurality of planar layers.

8. The system of claim 2, further comprising:
    a second resonant cavity having a second resonant frequency, wherein the second resonant cavity is electromagnetically coupled to the flow line so that the fluid within the flow line affects a frequency response of the second resonant cavity.

9. The system of claim 1, wherein the first resonant frequency is above 1 GHz.

10. A method for characterizing the dielectric response of a borehole fluid, the method comprising:
    receiving the borehole fluid into a portion of a flow line that is disposed proximate to a photonic bandgap (PBG) microwave resonant cavity so that a dielectric permittivity of the fluid affects a frequency response of the resonant cavity;
    providing electromagnetic waves in a microwave frequency range of 300 MHz to 300 GHz to the resonant cavity;
    measuring a first frequency response of the resonant cavity in response to the provided electromagnetic waves and in the presence of the borehole fluid in the flow line;
    determining a property of a first resonant mode of the resonant cavity using the first frequency response; and
    determining a property of the borehole fluid using the property of the first resonant mode.

11. The method of claim 10, wherein measuring the first frequency response comprises measuring at least one transmission coefficient from the resonant cavity by detecting at least a portion of the electromagnetic waves provided to the resonant cavity and by detecting at least a portion of the electromagnetic waves that are transmitted through the resonant cavity.

12. The method of claim 10, wherein the property of the first resonant mode is at least one of the resonant frequency of the first resonant mode and the quality factor of the first resonant mode.

13. The method of claim 10, wherein the first resonant mode of the resonant cavity is measured while the fluid is flowing through the flow line.

14. The method of claim 10, wherein the first resonant mode of the cavity is measured while the fluid is stationary in the flow line.

15. The method of claim 12, wherein the property of the fluid is a volume fraction of a component of the fluid in the flow line and the method further comprises determining the volume fraction of the component fluid using on at least one of the first resonant frequency and the first quality factor.

16. The method of claim 15, wherein the component fluid is at least one selected from a group consisting of water, emulsified brine, water based mud filtrate, oil based mud filtrate, dielectric marker, asphaltenes, resins, waxes, aromatics, saturates and gas.

17. The method of claim 10, further comprising:
    receiving the fluid into a portion of the flow line that is disposed proximate to a second PBG resonant cavity so that the dielectric permittivity of the fluid affects a frequency response of the second resonant cavity;
    providing electromagnetic waves to the second resonant cavity;
    measuring a second frequency response of the second resonant cavity in the presence of the fluid in the flow line;
    determining a property of a second resonant mode of the resonant cavity using the second frequency response; and
    determining a property of a component of the fluid in the flow line using the properties of the first resonant mode and the second resonant mode.

18. The method of claim 10, further comprising:
    using a plurality of PBG resonant cavities and a frequency response for each of the resonant cavities to determine a property for each resonant mode for each resonant cavity;
    determining a property of a component of the fluid using the properties for each resonant mode.

19. A method for characterizing the dielectric response of a fluid, the method comprising:
    receiving the fluid into a portion of a flow line that is disposed proximate to a photonic bandgap (PBG) resonant cavity so that a dielectric permittivity of the fluid affects a frequency response of the resonant cavity;
    providing electromagnetic waves to the resonant cavity;

measuring a first frequency response of the resonant cavity in the presence of the fluid in the flow line;

determining a property of a first resonant mode of the resonant cavity using the first frequency response; and determining a property of the fluid using the property of the first resonant mode, measuring a second frequency response, wherein the second frequency response is a frequency response of the resonant cavity or a second resonant cavity;

determining a property of a second resonant mode using the second frequency response; and determining a property of a component of the fluid in the flow line using the properties of the first resonant mode and the second resonant mode, wherein the property of the first resonant mode is at least one of the resonant frequency of the first resonant mode and the quality factor of the first resonant mode, wherein the property of the fluid is a volume fraction of a component of the fluid in the flow line and the method further comprises determining the volume fraction of the component fluid using on at least one of the first resonant frequency and the first quality factor.

20. The method of claim 19, wherein the property of the second resonant mode is at least one of the resonant frequency of the second resonant mode and the quality factor of the second resonant mode.

21. The method of claim 20, wherein the property of the component fluid is a volume fraction of the component fluid and the volume fraction is determined using the first resonant frequency and the second resonant frequency, the first quality factor, and the second quality factor.

22. The method of claim 20, further comprising:
determining a first real part of a first complex permittivity of the fluid using the first resonant frequency;
determining a second real part of a second complex permittivity of the fluid using the second resonant frequency;
determining a first imaginary part of a first complex permittivity of the fluid using the first quality factor;
determining a second imaginary part of a second complex permittivity of the fluid using the second quality factor; and
determining the volume fraction of the component fluid by computing a difference between the first real part of the first complex permittivity and the second real part of the second complex permittivity.

23. The method of claim 22, further comprising:
determining a conductivity of the component fluid using the volume fraction and the difference between the first imaginary part of the first complex permittivity and the second imaginary part of the second complex permittivity.

24. A system for characterizing a dielectric response of a borehole fluid, the system comprising:
a generator configured to generate electromagnetic waves in a microwave frequency range of 300 MHz to 300 GHz;
a photonic bandgap (PBG) microwave resonant cavity having a spatially localized resonant mode, wherein the resonant cavity is electromagnetically coupled to the generator such that the resonant cavity is configured to receive the electromagnetic waves;
a flow line disposed proximate to the resonant cavity so that the fluid, when contained within the flow line, affects a frequency response of the resonant cavity in response to the electromagnetic waves; and
a signal analyzer configured to measure the frequency response of the resonant cavity.

* * * * *